United States Patent
Michelson

[11] Patent Number: 6,136,001
[45] Date of Patent: Oct. 24, 2000

[54] APPARATUS AND METHOD FOR LINKING SPINAL IMPLANTS

[76] Inventor: Gary Karlin Michelson, 438 Sherman Canal, Venice, Calif. 90291

[21] Appl. No.: 09/126,585

[22] Filed: Jul. 31, 1998

Related U.S. Application Data

[63] Continuation of application No. 08/926,334, Sep. 5, 1997, which is a continuation of application No. 08/589,787, Jan. 22, 1996, abandoned, which is a continuation of application No. 08/219,626, Mar. 28, 1994, abandoned.

[51] Int. Cl.[7] .................................................. A61B 17/56
[52] U.S. Cl. .............................................................. 606/61
[58] Field of Search .................................. 606/61, 60, 72; 623/17, 16

[56] References Cited

U.S. PATENT DOCUMENTS

| | | |
|---|---|---|
| D. 281,814 | 12/1985 | Pratt et al. . |
| 350,420 | 10/1886 | Dillon . |
| 2,065,659 | 12/1936 | Cullen . |
| 2,181,746 | 11/1939 | Siebrandt . |
| 2,774,350 | 12/1956 | Cleveland, Jr. . |
| 3,298,372 | 1/1967 | Feinberg . |
| 3,426,364 | 2/1969 | Lumb . |
| 3,916,907 | 11/1975 | Peterson . |
| 4,047,524 | 9/1977 | Hall .......................................... 606/61 |
| 4,271,832 | 6/1981 | Evans et al. . |
| 4,289,123 | 9/1981 | Dunn . |
| 4,401,112 | 8/1983 | Rezaian . |
| 4,439,152 | 3/1984 | Small . |
| 4,554,914 | 11/1985 | Kapp et al. . |
| 4,570,623 | 2/1986 | Ellison et al. . |
| 4,570,624 | 2/1986 | Wu . |
| 4,592,346 | 6/1986 | Jurgutis . |
| 4,599,086 | 7/1986 | Doty . |
| 4,604,995 | 8/1986 | Stephens et al. . |
| 4,611,581 | 9/1986 | Steffee . |

(List continued on next page.)

FOREIGN PATENT DOCUMENTS

| | | |
|---|---|---|
| 0 179 695 | 4/1986 | European Pat. Off. . |
| 0 551 187 A1 | 7/1993 | European Pat. Off. . |
| 0 552 109 A1 | 7/1993 | European Pat. Off. . |
| 2 709 410 A1 | 3/1995 | France . |
| 106 101 | 10/1942 | Germany . |
| 3132520 A1 | 6/1982 | Germany . |
| 2 048 671 | 3/1994 | Spain . |
| 1107854 | 8/1984 | U.S.S.R. . |

OTHER PUBLICATIONS

Rathke, F.W., et al.; Surgery of the Spine; Atlas of Orthopaedic Operations, vol. 1, p. 137, W.B. Saunders Co., Philadelphia (1979).

Morscher, E., et al.; Die vordere Verplattung der Halswirbelsäule mit dem Hohlschrauben–Plattensystem aus Titanium, *Der Chirurg*, vol. 57, pp. 702–707 (1986) with English Translation.

*Primary Examiner*—Michael Buiz
*Assistant Examiner*—(Jackie) Tan-Uyen T. Ho
*Attorney, Agent, or Firm*—Martin & Ferraro, LLP

[57] ABSTRACT

A spinal fixation device for stabilizing one or more segments of the human spine and for preventing the dislodgement of intervertebral spinal fusion implants, which remains permanently fixated once applied. The spinal fixation device of the present invention comprises of a staple member made of material appropriate for human surgical implantation which is of sufficient length to span the disc space between two adjacent vertebrae and to engage, via essentially perpendicular extending projections, the vertebrae adjacent to that disc space. A portion of the staple of the spinal fixation device interdigitates with an already implanted intervertebral spinal fusion implant which itself spans the disc space to engage the adjacent vertebrae, and the spinal fixation deice is bound to the spinal fusion implant by a locking means. The spinal fixation device of the present invention is of great utility in restraining the vertebrae adjacent to the spinal fusion implant from moving apart as the pine is extended and also serves as an anchor for a multi-segmental spinal alignment means for aligning more that one segment of the spine.

126 Claims, 10 Drawing Sheets

U.S. PATENT DOCUMENTS

| | | |
|---|---|---|
| 4,696,290 | 9/1987 | Steffee . |
| 4,743,256 | 5/1988 | Brantigan . |
| 4,743,260 | 5/1988 | Burton . |
| 4,759,769 | 7/1988 | Hedman et al. . |
| 4,805,602 | 2/1989 | Puno et al. . |
| 4,878,915 | 11/1989 | Brantigan . |
| 4,903,882 | 2/1990 | Long . |
| 4,913,144 | 4/1990 | Del Medico . |
| 4,960,420 | 10/1990 | Goble et al. . |
| 5,015,247 | 5/1991 | Michelson . |
| 5,084,048 | 1/1992 | Jacob et al. .............................. 606/61 |
| 5,092,893 | 3/1992 | Smith . |
| 5,108,422 | 4/1992 | Green et al. . |
| 5,258,031 | 11/1993 | Salib et al. . |
| 5,314,427 | 5/1994 | Goble et al. . |
| 5,352,229 | 10/1994 | Goble et al. . |
| 5,364,399 | 11/1994 | Lowery et al. . |
| 5,395,372 | 3/1995 | Holt et al. . |
| 5,556,431 | 9/1996 | Butter-Janz . |
| 5,562,663 | 10/1996 | Wisnewski et al. . |

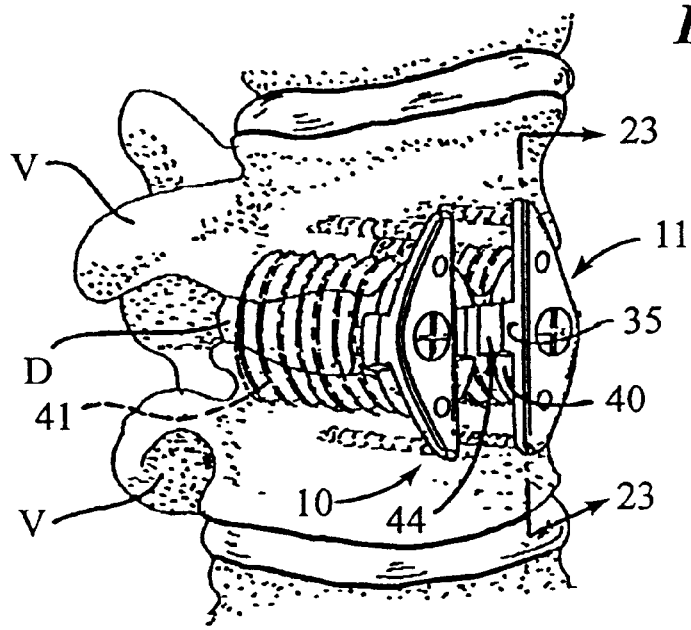
Fig. 1
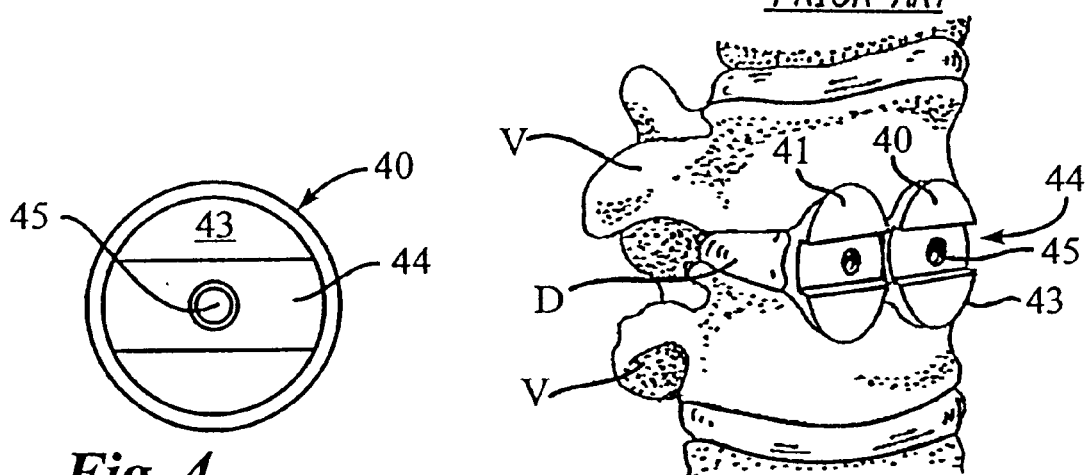
Fig. 2
PRIOR ART
Fig. 4
PRIOR ART
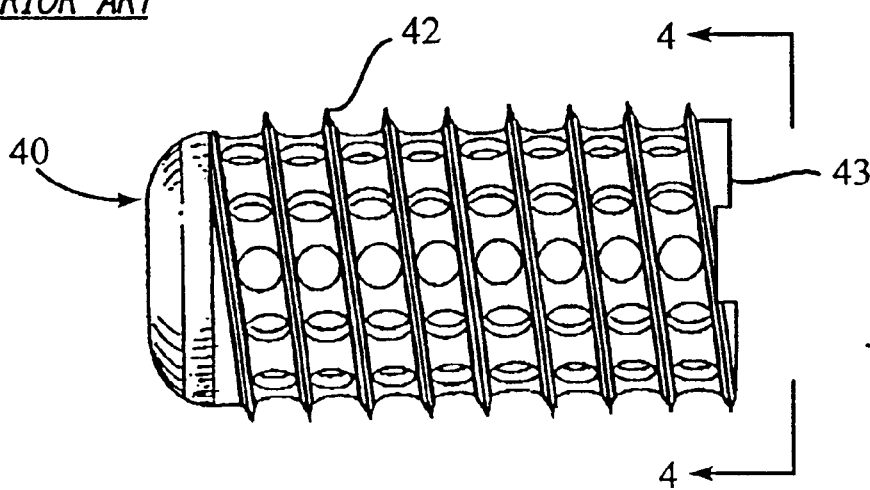
Fig. 3
PRIOR ART

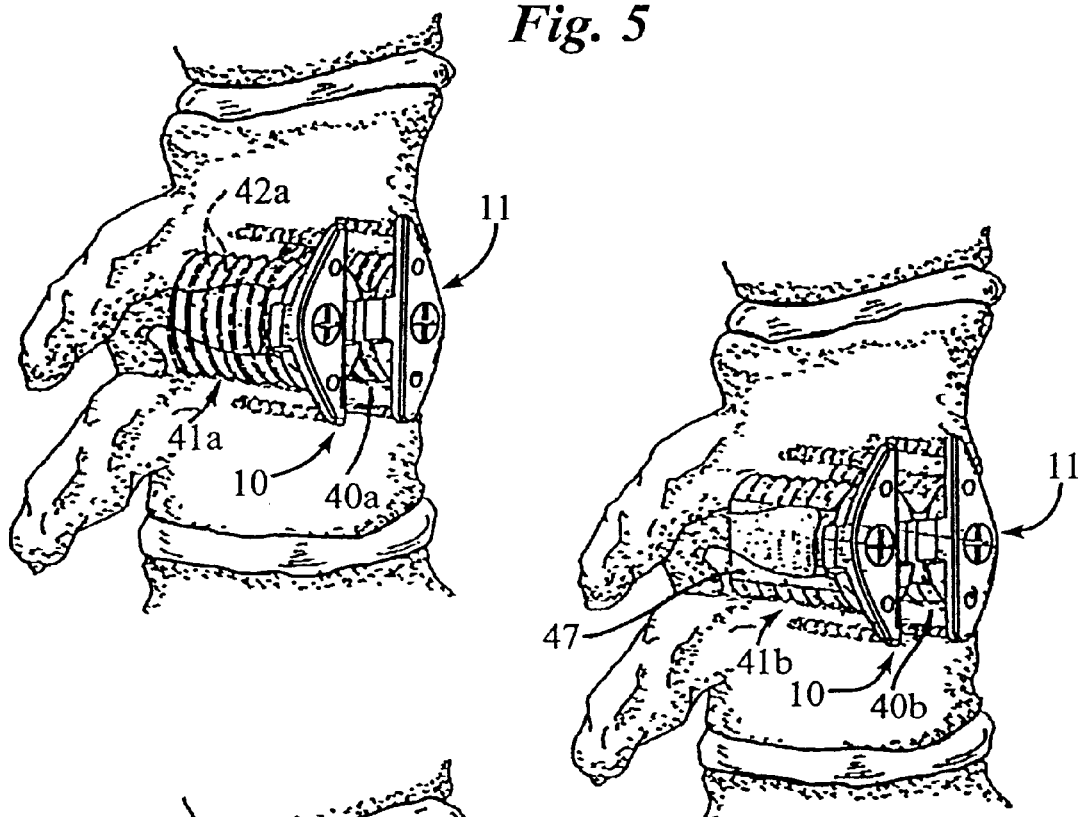
Fig. 5
Fig. 6
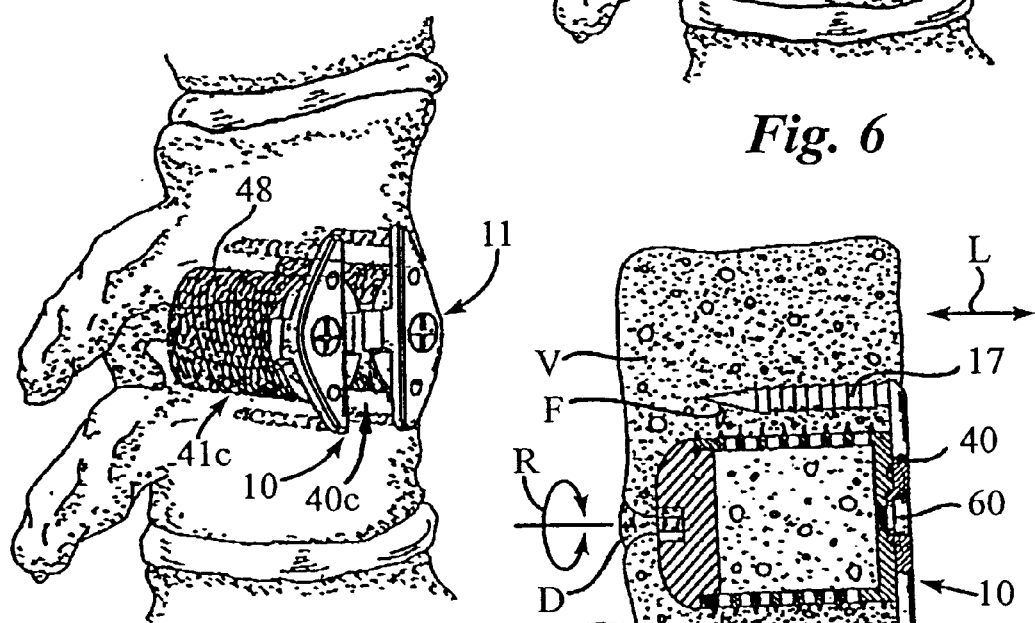
Fig. 7
Fig. 12

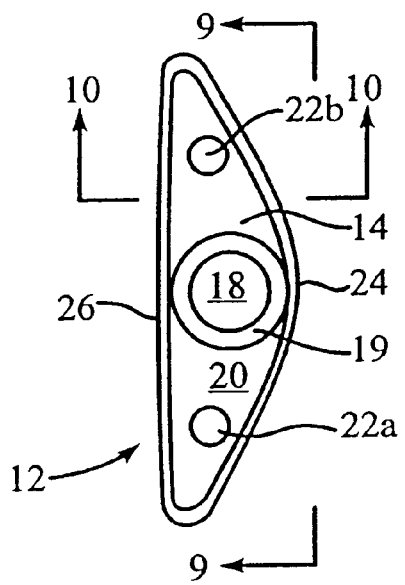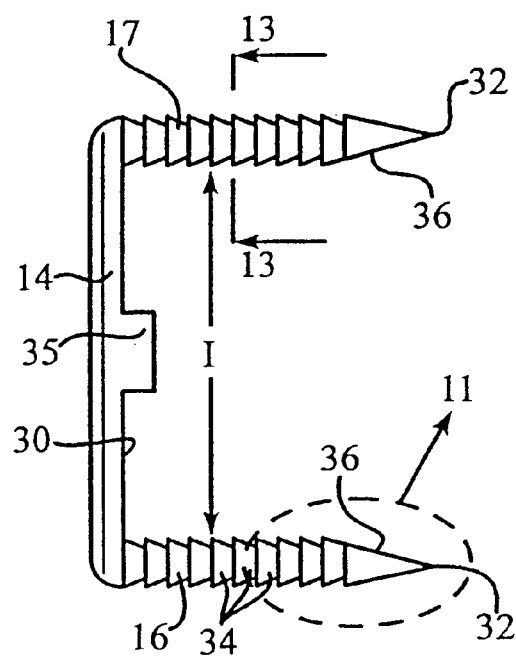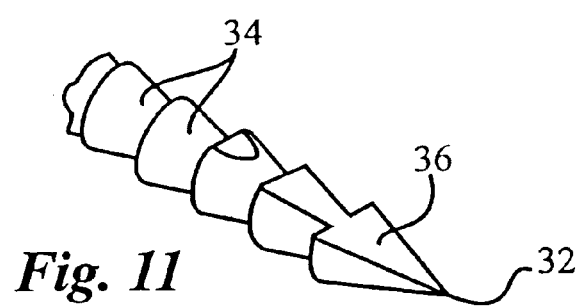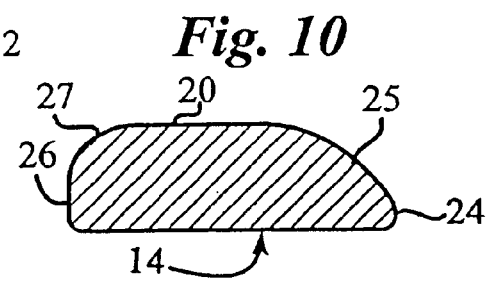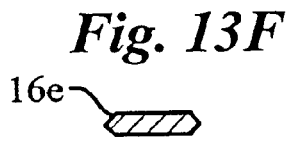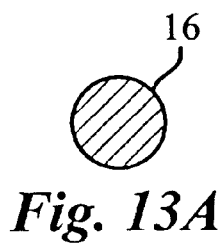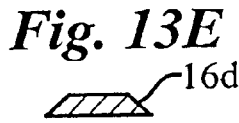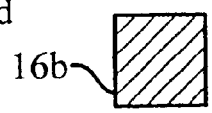

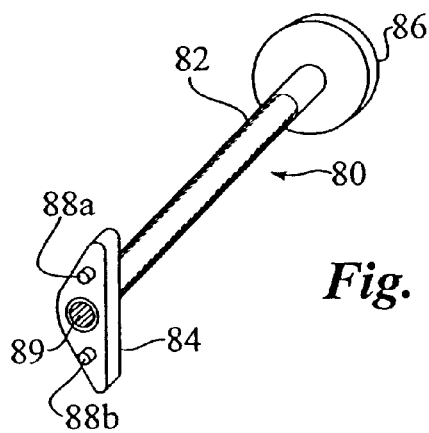
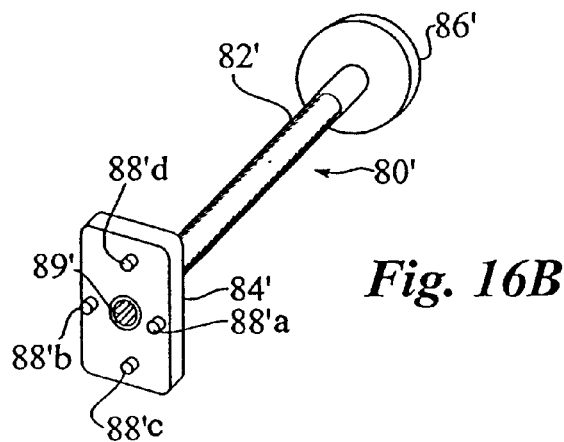
*Fig. 16A*   *Fig. 16B*
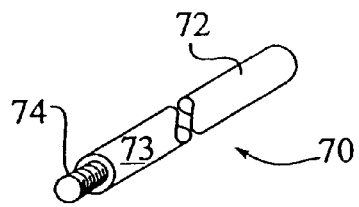
*Fig. 17A*
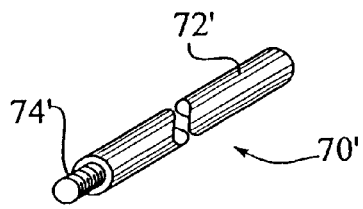
*Fig. 17B*
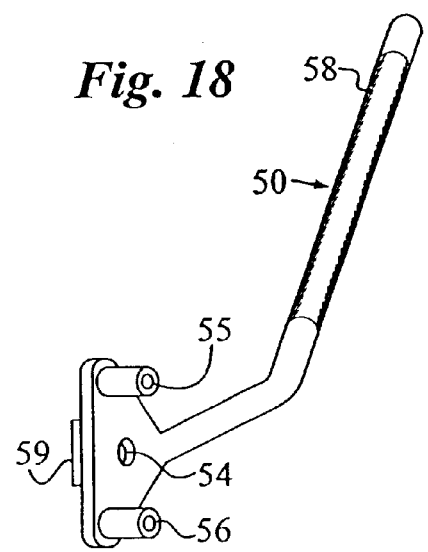
*Fig. 18*

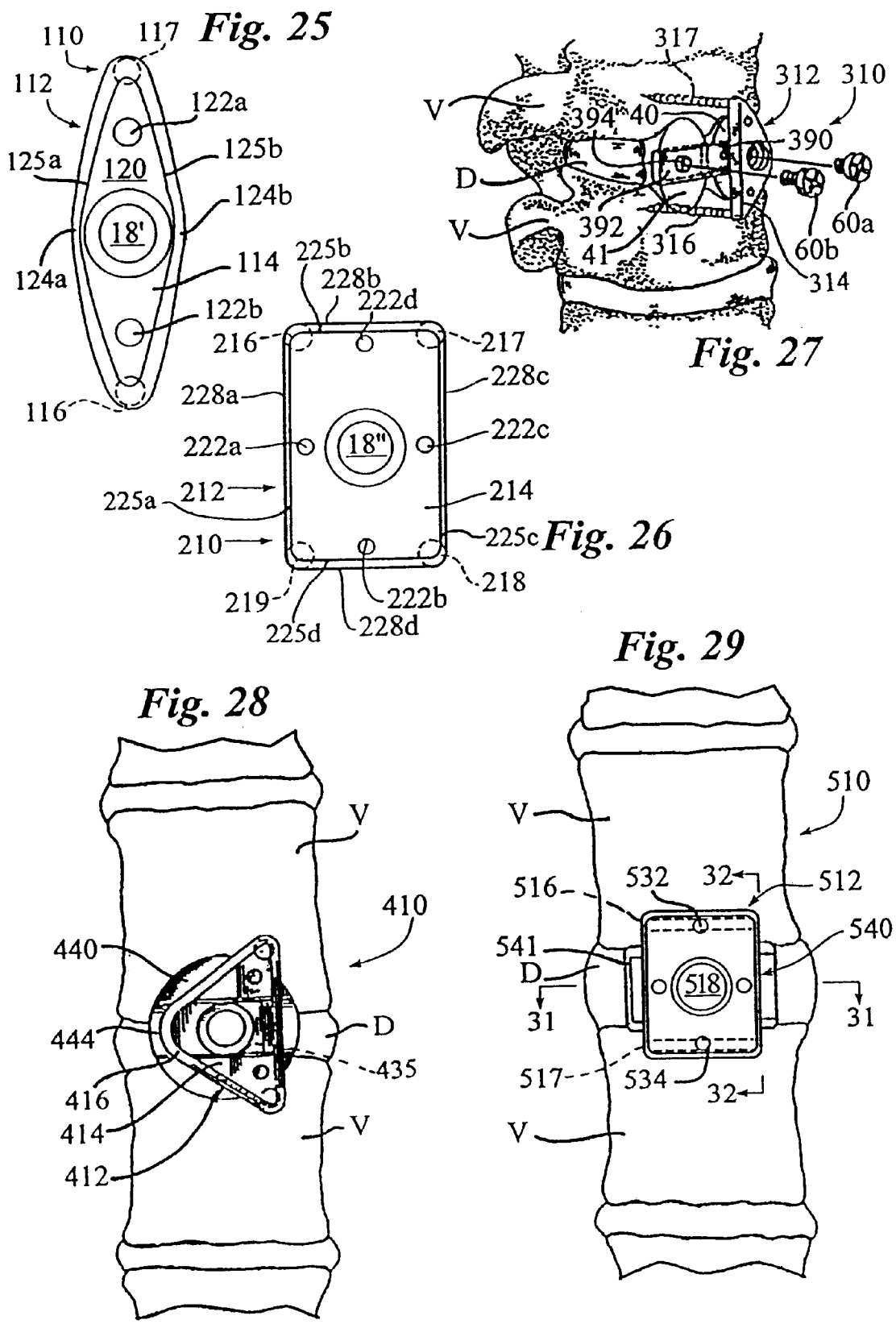

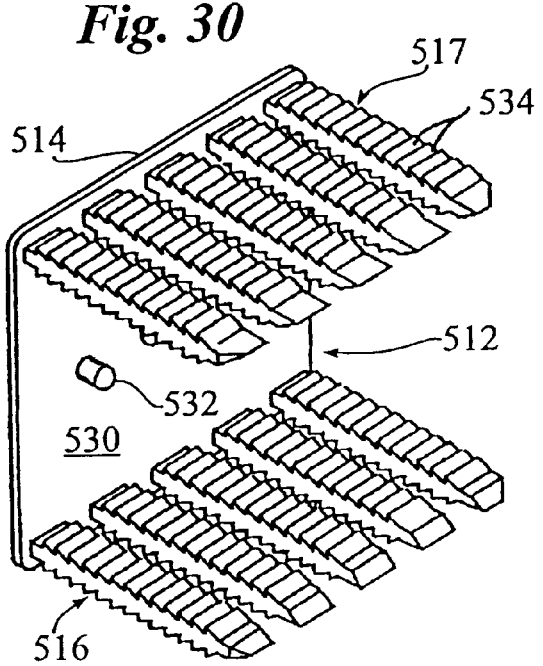
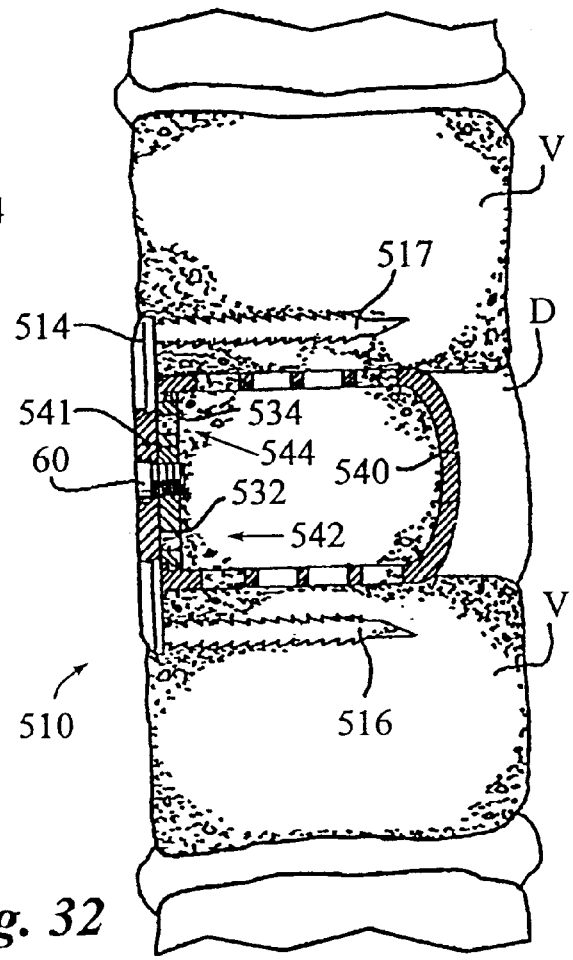
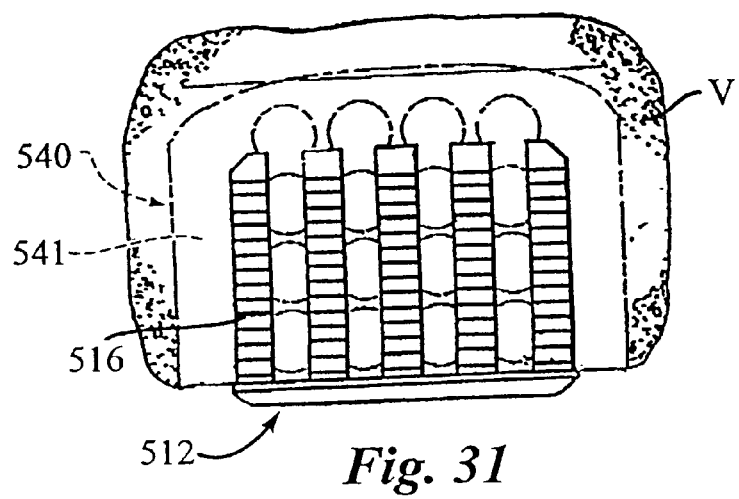

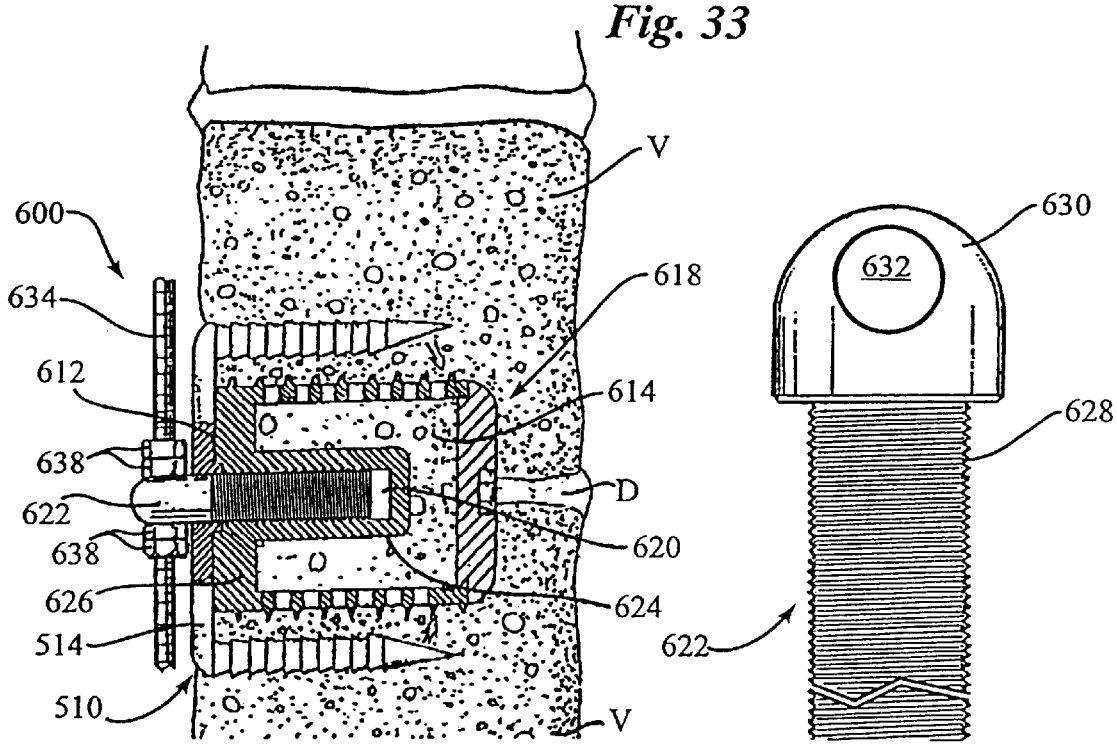
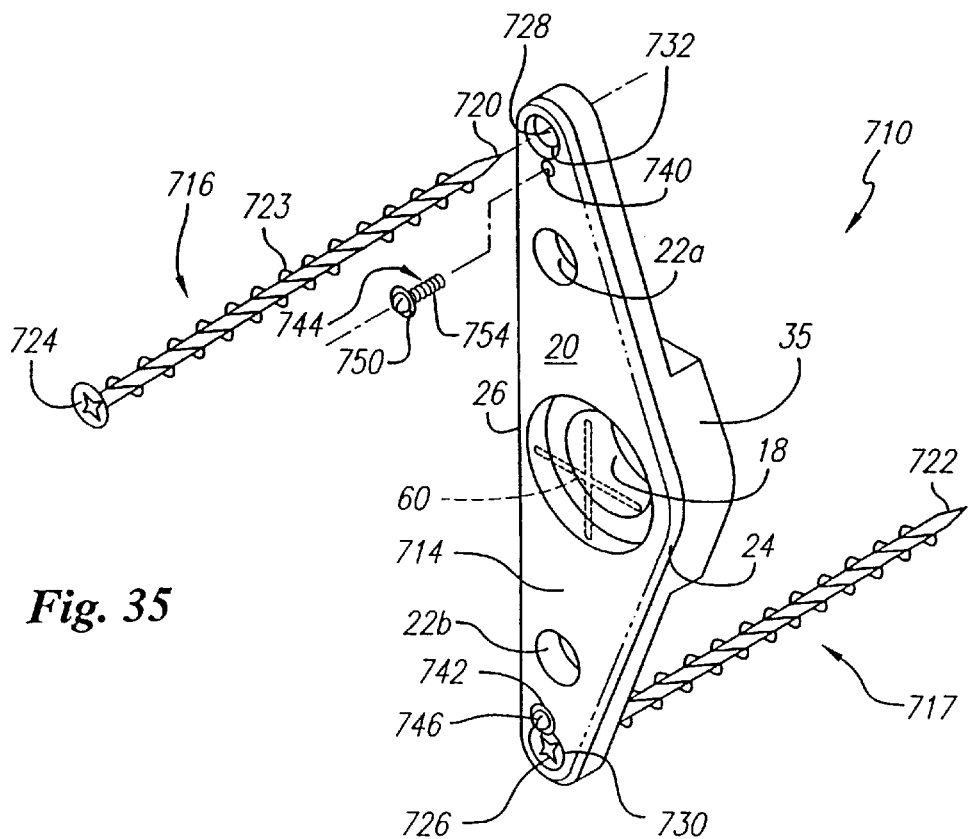

APPARATUS AND METHOD FOR LINKING SPINAL IMPLANTS

This is a continuation of application Ser. No. 08/926,334, filed Sep. 5, 1997, which is a continuation of Ser. No. 08/589,787 abandoned filed Jan. 22, 1996 which is a continuation of 08/219,626 abandoned filed Mar. 28, 1994.—all of which are incorporated herein by reference.

BACKGROUND OF THE INVENTION

1. Field of the Invention

This invention relates to surgical interbody fixation devices and in particular to a surgically implantable device for the stabilization of adjacent vertebrae of the human spine undergoing spinal arthrodesis and for the prevention of the dislodgement of spinal fusion implants used in the fusion process.

2. Description of the Related Art

When a segment of the human spine degenerates, or otherwise becomes diseased, it may become necessary to surgically remove the affected disc of that segment, and to replace it with bone for the purpose of obtaining a spinal fusion by which to restore more normal, pre-morbid, spatial relations, and to provide for enhanced stability across that segment. Performing such surgery of the spine from an anterior (front) approach offers the great advantage of avoiding the spinal cord, dural sac, and nerve roots. Unfortunately, in entering the disc space anteriorly a very important band-like structure called the anterior longitudinal ligament, is violated. This structure physiologically acts as a significant restraint resisting the anterior displacement of the disc itself and acting as a tension band binding the front portions of the vertebrae so as to limit spinal hyperextension.

Historically, various devices have been utilized in an attempt to compensate for the loss of this important stabilizing structure. These devices have assumed the form of blocks, bars, cables, or some combination thereof, and are bound to the vertebrae by screws, staples, bolts, or some combination thereof. The earliest teachings are of a metal plate attached to adjacent vertebrae with wood-type screws. Dryer teaches the use of a staple-screw combination. Brantigan U.S. Pat. No. 4,743,256 issued on May 10, 1988, teaches the use of a block inserted to replace the disc, affixed to a plate then screwed to the vertebrae above and below. Raezian U.S. Pat. No. 4,401,112 issued on Aug. 30, 1993, teaches the use of a turnbuckle affixed to an elongated staple such that at least one entire vertebral body is removed, the turnbuckle portion is placed within the spine, and the staple extends both above and below the turnbuckle and engages the adjacent vertebrae to the one removed.

Unfortunately, both staples and screws have quite predictably demonstrated the propensity to back out from the vertebrae. This is quite understandable as any motion, either micro or macro, tends to stress the interface of the metallic implant to the bone, and in doing so causes the bone to relieve the high stress upon it by resorbing and moving away from the metal. This entropic change is universally from the more tightened and thus well-fixated state, to the less tightened and less fixated state. For a staple, this is specifically from the more compressed and engaged state, to the less compressed and disengaged state. Similarly, screws in such a dynamic system loosen and back out.

The potential consequences of such loosening and consequent backing out of the hardware from the anterior aspect of the vertebral column may easily be catastrophic. Because of the proximity of the great vessels, aortic erosions and perforations of the vena cava and iliac vessels have usually occurred with unfortunate regularity and have usually resulted in death.

Therefore, the need exists for a device which is effective in restoring stability to a segment of the spine such as, but not limited to, the anterior aspect of the human spine and which will without danger remain permanently fixated once applied.

SUMMARY OF THE INVENTION

The present invention is directed to a spinal fixation device for stabilizing a segment of the human spine and for preventing the dislodgement of intervertebral spinal fusion implants, which remains permanently fixated to the spine once applied. The spinal fixation device of the present invention comprises a staple member made of a material appropriate for human surgical implantation and which is of sufficient length to span the disc space between two adjacent vertebrae. The staple member engages, via essentially perpendicular extending projections, the vertebrae adjacent to that disc space. The projections are sharpened and pointed so as to facilitate their insertion into the vertebrae and are segmented or ratcheted to prevent the staple member from disengaging and backing out once inserted.

In the preferred embodiment of the spinal fixation device of the present invention, a portion of the staple member interdigitates with an already implanted intervertebral spinal fusion implant and the staple member is bound to the spinal fusion implant by a locking mechanism such as a screw with a locking thread pattern. The anchoring of the staple member via a locking mechanism to a spinal fusion implant protects the patient from the danger of the staple member itself disengaging and backing out. Further, if the spinal fusion implant is externally threaded, such as the spinal fusion implant taught by Michelson, U.S. Pat. No. 5,015,247 issued on May 14, 1991, then the staple member could only back out if the spinal fusion implant were free to rotate. However, the rotation of the spinal fusion implant in this instance is blocked by its connection to the staple member which is fixated across the disc space in such a way as to be incapable of rotation. Thus, the staple member is made safe against dislodgement by attachment to the spinal fusion implant and the stability of the spinal fusion implant is assured as it is also stabilized by the staple member and each works in connection with the other to remove the only remaining degree of freedom that would allow for the disengagement of either.

The spinal fixation device of the present invention is broadly applicable to the anterior, posterior and lateral aspects of the spinal column, be it the cervical, thoracic or lumbar area. In particular, the use of a staple member spanning the disc space and engaging the adjacent vertebrae which is applied to the anterior aspect of the spine is of great utility in restraining those vertebral bodies from moving apart as the spine is extended and thus is effective in replacing the anterior longitudinal ligament of the patient.

The spinal fixation device of the present invention provides the advantage of facilitating cross vertebral bony bridging (fusion via immobilization) which when achieved relieves all of the forces on the inserted spinal fusion implants. The spinal fixation device of the present invention may be coated with materials to promote bone fusion and thus promote the incorporation and ultimate entombment of the spinal fixation device into the bone fusion mass. The use of a bone fusion promoting material results in a speedier vertebra to vertebra fusion as bone may grow along the coated spinal fixation device bridging the two vertebrae so that the spinal fixation device acts as a trellis and supplies essential chemical elements to facilitate the bone fusion process.

Another advantage provided by the spinal fixation device of the present invention is that as it is inserted it compresses the adjacent vertebrae together, thus increasing the compressive load on the spinal fusion implants or implants within the disc space, such compression being beneficial to fusion and further stabilizing the spinal fusion implants.

A further advantage of the spinal fixation device of the present invention is that it may be used as an anchor such that a multiplicity of spinal fixation devices may then be interconnected via a cable, rod, bar, or plate, so as to achieve or maintain a multi-segmental spinal alignment.

Alternatively, the spinal fixation device of the present invention could be made of resorbable materials, such as bio-compatible resorbable plastics, that resorb at an appropriate rate such that once the spinal fixation device is no longer needed (i.e. when spinal fusion is complete) the body would resorb the spinal fixation device. The spinal fixation device could be only in part resorbable such that the projections of the staple member would be non-resorbable and would remain incarcerated in the vertebrae and sealed off once the resorbable portion of the staple is resorbed by the body.

As a further alternative, the spinal fixation device of the present invention could be made wholly of in part of ceramic and more particularly made of or coated with a ceramic such as hydroxyapatite that would actively participate in the fusion process.

OBJECTS OF THE PRESENT INVENTION

It is an object of the present invention to provide a spinal fixation device having a staple member spanning the disc space and engaging two adjacent vertebrae of the spine to restrain the vertebrae from moving apart as the spine is extended;

It is an another object of the present invention to provide a spinal fixation device that is effective in replacing the function of the anterior longitudinal ligament of a patient;

It is a further object of the present invention to provide a means for protecting the patient from the danger of the spinal fixation device itself disengaging and backing out by its being anchored to an intervertebral spinal fusion implant;

It is still another object of the present invention to provide a spinal fixation device that blocks the rotation of an intervertebral spinal fusion implant by its connection to the staple member which is fixated across the disc space in such a way as to be incapable of rotation thereby preventing the spinal fusion implant from backing out;

It is yet another object of the present invention to provide a spinal fixation device that is broadly applicable to the anterior aspect of the spinal column, be it the cervical, thoracic or lumbar area;

It is another object of the present invention to provide a spinal fixation device which may be applied longitudinally at any point about the circumference of the anterior aspect of the spine;

It is also another object of the present invention to provide a spinal fixation device that stabilizes a surgically implanted spinal fusion implant and works in connection with the spinal fusion implant to prevent disengagement of either;

It is another object of the present invention to provide a spinal fixation device that achieves cross vertebral bony bridging (fusion) which ultimately relieves all of the forces on inter-vertebral spinal fusion implants inserted within the disc space between two adjacent vertebrae, and provides for a permanently good result;

It is another object of the present invention to provide a spinal fixation device that serves as an anchor, such that a multiplicity of these anchors may then be interconnected via a cable, rod, bar, or plate, so as to achieve or maintain a multi-segmental spinal alignment; and It is a further object of the present invention to provide a spinal fixation device that directly participates in the bony bridging of two adjacent vertebrae and participates in the spinal fusion process across those vertebrae.

These and other objects of the present invention will become apparent from a review of the accompanying drawings and the detailed description of the drawings.

BRIEF DESCRIPTION OF THE DRAWINGS

FIG. 1 is a perspective side view of a segment of the spinal column having two spinal fusion implants shown partially in hidden line inserted across the disc space between two adjacent vertebrae with each spinal fusion implant having a spinal fixation device of the present invention shown partially in hidden line secured thereto, spanning across the disc space and inserted into the vertebrae.

FIG. 2 is a perspective side view of a segment of the spinal column having two spinal fusion implants inserted across the disc space between two adjacent vertebrae.

FIG. 3 is an elevational side view of a cylindrical threaded spinal fusion implant.

FIG. 4 is an end view of the cylindrical threaded spinal fusion implant along lines 4—4 of FIG. 3.

FIG. 5 is a perspective side view of a segment of the spinal column having two non-threaded spinal fusion implants with external ratchetings, shown in hidden line, inserted across the disc space between two adjacent vertebrae with each spinal fusion implant having a spinal fixation device of the present invention, shown partially in hidden line, coupled thereto, spanning across the disc space and inserted into the vertebrae.

FIG. 6 is a perspective side view of a segment of the spinal column having two spinal fusion implants having truncated sides with external ratchetings shown in hidden line inserted across the disc space between two adjacent vertebrae with each spinal fusion implant having a spinal fixation device of the present invention shown partially in hidden line coupled thereto, spanning across the disc space and inserted into the vertebrae.

FIG. 7 is a perspective side view of a segment of the spinal column having two spinal fusion implants having a knurled external surface shown in hidden line inserted across the disc space between two adjacent vertebrae with each spinal fusion implant having a spinal fixation device of the present invention shown partially in hidden line coupled thereto, spanning across the disc space and inserted into the vertebrae.

FIG. 8 is a top plan view of the spinal fixation device of the present invention.

FIG. 9 is a side view of the spinal fixation device of the present invention along lines 9—9 of FIG. 8.

FIG. 10 is a cross sectional view taken along lines 10—10 of FIG. 8 showing the top member of the spinal fixation device of the present invention.

FIG. 11 is an enlarged fragmentary perspective side view of a projection of the spinal fixation device of the present invention taken along line 11 of FIG. 9.

FIG. 12 is a cross sectional view of the spinal fixation device of the present invention inserted into the vertebrae and secured to the spinal fusion implant with the arrows showing the forces exerted, the rotational axis and the longitudinal axis of the spinal fusion implant.

FIG. 13A is a cross sectional view along line 13—13 of FIG. 9 of the preferred embodiment of the projections of the present invention.

FIGS. 13B, 13C, 13D, 13E, and 13F are cross sectional views taken along line 13—13 of FIG. 9 showing alternative embodiments of the projections of the spinal fixation device of the present invention.

FIG. 16A is a perspective side view of the instrumentation used for driving the spinal fixation device of the present invention into the vertebrae.

FIG. 16B is a perspective side view of a first alternative embodiment of the instrumentation used for driving the spinal fixation device of the present invention into the vertebrae.

FIG. 17A is a perspective side view of an alignment rod used to align the spinal fixation device of the present invention.

FIG. 17B is a perspective side view of an alternative embodiment of the alignment rod having splines used to align the spinal fixation device of the present invention.

FIG. 18 is a front perspective view of the drill template instrument.

FIG. 25 is a top plan view of a first alternative embodiment of the spinal fixation device of the present invention.

FIG. 26 is a top plan view of a second alternative embodiment of the spinal fixation device of the present invention.

FIG. 27 is a perspective side view of a third alternative embodiment of the spinal fixation device of the present invention coupled to two spinal fusion implants and inserted in adjacent vertebrae of the spinal column.

FIG. 28 is a top plan view of a fourth alternative embodiment of the spinal fixation device of the present invention inserted into the vertebrae of the spinal column having a spinal fusion implant inserted in the disc space.

FIG. 29 is a top plan view of a fifth alternative embodiment of the spinal fixation device of the present invention inserted into the vertebrae of the spinal column having a spinal fusion implant inserted in the disc space.

FIG. 30 is a perspective bottom view of the fourth alternative embodiment of the spinal fixation device of the present invention.

FIG. 31 is a cross sectional view along lines 31—31 of FIG. 29 showing the fifth alternative embodiment of the spinal fixation device of the present invention inserted into the adjacent vertebrae and coupled to a spinal fusion implant.

FIG. 32 is a cross sectional view along lines 32—32 of FIG. 29 showing the projections of the fifth alternative embodiment of the present invention with respect to a spinal fusion implant inserted within the disc space.

FIG. 33 is a cross sectional view of a spinal fixation device of the present invention engaging two adjacent vertebrae and being attached to a spinal fusion implant, shown being used as an anchor for a multi-segmental spinal alignment means.

FIG. 34 is an enlarged elevational side view of a threaded post used to connect the spinal fixation device of the present invention to a multi-segmental spinal alignment means.

FIG. 35 is an exploded perspective view of a sixth alternative embodiment of the spinal fixation device of the present invention having independent projection members that are screws.

DETAILED DESCRIPTION OF THE DRAWINGS

Figure 14:
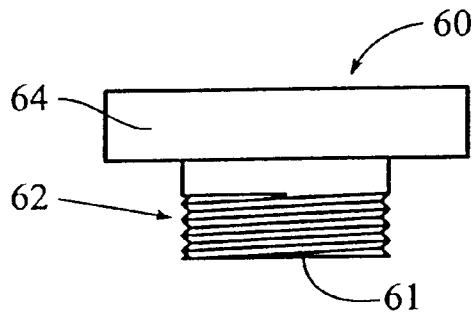
FIG. 14 is an enlarged elevational side view of the locking screw used to secure the spinal fixation device of the present invention to a spinal fusion implant.

Referring to FIG. 1 and 2, two identical spinal fixation devices of the present invention, each being generally referred to by the numerals 10 and 11, respectively, are shown inserted into two vertebrae V adjacent to a disc D of a segment of the human spine. Each spinal fixation device 10 and 11 is shown coupled to identical spinal fusion implants 40 and 41 that have been surgically implanted in the disc space between adjacent vertebrae V. In this manner, the spinal fixation devices 10 and 11 stabilize a segment of the spine, prevent the dislodgement of the spinal fusion implant 40, and remain permanently fixated to the spine once applied. The spinal fixation devices 10 and 11 are identical such that the description of one is equally applicable to the other. Thus, the description that follows will be directed to spinal fixation device 10.

Referring to FIGS. 3–4, the spinal fusion implant 40 such as, but not limited to, the spinal fusion implant described by Michelson, U.S. Pat. No. 5,015,247 issued on May 14, 1991, is shown. The spinal fusion implant 40 is cylindrical in shape and has external threads 42 at its outer perimeter for engaging the bone of the vertebrae V adjacent to the disc D. The spinal fusion implant 40 has an insertion end 43 having a depression 44 and a threaded aperture 45 for engaging a portion of the spinal fixation device 10 and also for engaging a portion of an instrument used to insert the spinal fixation device 10 into the vertebrae V.

Referring to FIGS. 5–7, it is appreciated that the spinal fixation devices 10 and 11 of the present invention are not limited in use with a threaded spinal fusion implant 40 and 41, but may be used with different types of spinal fusion implants. For example, the spinal fixation devices 10 and 11 may be coupled to spinal fusion implants 40a and 41a, respectively, each having external ratchetings 42a instead of external threads 42 as shown in FIG. 5. Alternatively, the spinal fixation devices 10 and 11 may be coupled to spinal fusion implants 40b and 41b, respectively, each having a partially cylindrical shape with at least one truncated side 47 as shown in FIG. 6. As a further alternative, the spinal fixation devices 10 and 11 may be coupled to spinal fusion implants 40c and 41c, respectively, each having a knurled external surface 48 as shown in FIG. 7. It is also appreciated that the spinal fixation devices may be used with a variety of other bone fusion implants without departing from the scope of the present invention.

Referring to FIGS. 8–9, in the preferred embodiment, the spinal fixation device 10 of the present invention comprises a staple member 12 having a substantially planar top member 14 which is of sufficient length to span one intervertebral disc D and to engage, via a plurality of essentially perpendicular extending projections 16 and 17, the vertebrae V adjacent to that disc D. The top member 14 has a central opening 18 within a concentric, countersunk recess 19 for receiving therethrough a screw or similar coupling means for coupling the spinal fixation device 10 to the spinal fusion implant 40. The top member 14 has an upper surface 20 having a pair of openings 22a and 22b for receiving the posts 88a and 88b of a driving instrument 80 which is described in greater detail below in reference to FIGS. 16A and 16B.

Referring to FIG. 10, a cross sectional view of the top member 14 is shown. In the preferred embodiment, the top member 14 is generally triangularly shaped and is radiused along curved side 24 and straight side 26. The curved side 24 of the top member 14 is radiused at its upper edge 25 and at the upper edge 27 of straight side 26 to conform to the external curvature of the vertebrae V. In this manner, smooth surfaces are created at the upper edges 25 and 27 of the top member 14 that are contoured to the shape of the external curvature of the vertebrae V when the staple member 12 is in place. The smooth contoured surface of the upper edges 25 and 27 of the top member 14 prevent aortic erosions and perforations of the vessels proximate the vertebral column such as the vena cava and the iliac vessels which might otherwise result from friction.

In the preferred embodiment of the spinal fixation device 10, the top member 14 has a width ranging from 6.0 mm to 28.0 mm, with 10.0 mm being the preferred width, and having a thickness in the range of 2.0 mm to 4.0 mm, with 3.0 mm being the preferred thickness. The staple member 12 is made of material appropriate for human surgical implantation including all surgically appropriate metals such as but not limited to, titanium, titanium alloy, chrome molybidium alloys, stainless steel; or non-metallic materials including permanent or resorbable substances or composites, carbon fiber materials, resins, plastics, ceramics or others.

Further, the staple member 12 of the present invention may be treated with, or even composed of, materials known to participate in or promote in the fusion process or bone growth. The spinal fixation device 10 may be coated with materials to promote bone fusion and thus promote the incorporation and ultimate entombment of the spinal fixation device 10 into the bone fusion mass. The use of a bone fusion promoting material such as, but not limited to hydroxyapatite, hydroxyapatite tricalcium phosphate or bone morphogenic protein, results in a speedier vertebra V to vertebra V fusion as bone may grow along the coated spinal fixation device 10 bridging the two vertebrae V so that the spinal fixation device 10 acts as a trellis and supplies essential chemical elements to facilitate the bone fusion process.

Referring again to FIG. 9, the projections 16 and 17 are positioned at opposite ends of the top member 14 and depend downwardly and extend perpendicularly from the bottom surface 30 of the top member 14. The projections 16 and 17 each terminate in a distal end 32 that is pointed and sharpened to facilitate the insertion of the projections 16 and 17 into the vertebrae V.

The staple member 12 is most effective when the interprojection distance I between projections 16 and 17 is at least 4.0 mm and preferably 6.0 mm greater than the diameter of the particular spinal fusion implant 40 for which the spinal fixation device 10 is being used so that at least 2.0 mm and preferably 3.0 mm of bone from the vertebrae V will be present between the spinal fusion implant 40 and each of the projections 16 and 17. Typically, intervertebral spinal fusion implants have a diameter that ranges from 12.0 mm to 28.0 mm, therefore, the interprojection distance I typically will range from 18.0 mm to 34.0 mm for most applications.

In the preferred embodiment, the projections 16 and 17 comprise a series of segmented and ratcheted portions 34. The segmented and ratcheted portions 34 provide for a "one way" insertion of the staple member 12 to prevent the backing-out of the projections 16 and 17 once they are inserted into the bone of the vertebrae V. In the preferred embodiment, each segmented and ratcheted portion 34 of the projections 16 and 17 is conical in shape and the diameter of each segmented and ratcheted portion 34 increases in the direction from the distal end 32 toward the top member 14 so that the projections 16 and 17 resemble a stack of cones. The segmented and ratcheted portions 34 are spaced approximately 2.0 mm to 4.0 mm apart, with 3.0 mm being the preferred distance between each segmented and ratcheted portion 34.

Referring to FIG. 11–12, in the preferred embodiment of the spinal fixation device 10, in order to further facilitate the insertion of the projections 16 and 17 into the vertebrae V, the distal end 32 of each projection 16 has an eccentric, incline-planed inner surface 36 as shown in FIG. 11. The eccentric, incline-planed inner surface 36 of each of the projections 16 and 17 create a force F which pushes the bone of the vertebrae V toward the spinal fusion implant 40 as the staple member 12 is inserted into each of the vertebrae V as shown in FIG. 12.

Referring to FIGS. 13A–13F, in the preferred embodiment of the spinal fixation device 10, the projections 16 and 17 are cylindrical in shape having a circular cross section as shown for projection 16 in FIG. 13A. Alternatively, the projection 16a may have a triangular cross section as shown in FIG. 13B; the projection 16b may have a square cross section as shown in FIG. 13C; the projection 16c may have a rectangular cross section as shown in FIG. 13D; the projection 16d may have a trapezoidal cross section as shown in FIG. 13E; or the projection 16e may have a cross section with a configuration as shown in FIG. 13F.

In the preferred embodiment, the projections 16 and 17 each have a diameter of approximately 2.0 mm to 4.0 mm, with 3.0 mm being the preferred diameter at the widest point. The projection 16 and 17 each have a length ranging from 16.0 mm to 28.0 mm, with 22.0 mm being the preferred length when the spinal fixation device 10 is implanted in the direction of the anterior aspect of the vertebra V to the posterior aspect of the vertebrae V. Alternatively, it is appreciated that the projections 16 and 17 each could have a longer length depending on the diameter of the vertebrae V in which the projections 16 and 17 are implanted.

Referring again to FIG. 9, the top member 14 of the staple member 12 has a central bar 35 extending from the center of its bottom surface 30, for interdigitating and mating to an already implanted intervertebral spinal fusion implant 40. In the preferred embodiment, the central bar 35 has a thickness in the range of 0.5 mm to 1.5 mm, with 0.5 mm being the preferred thickness.

Referring to FIG. 1, the central bar 35 is configured so that it complements and engages the depression 44 at the insertion end 43 of the spinal fusion implant 40. Once engaged to the depression 44, the bar 35 interdigitates with the depression 44 of the spinal fusion implant 40 to lock and prevent the rotation of the spinal fusion implant 40.

Referring to FIG. 14, in the preferred embodiment, the staple member 12 is secured to the spinal fusion implant 40 by a screw 60 having threaded end 61 with a locking thread pattern 62 and screw head 64. The locking thread pattern 62 has a reduced pitch at the bottom of the threaded end 61 such that the screw 60 is self-locking. However, it is appreciated that the threaded pattern 62 may be any of the means for locking a screw well known by those skilled in the art.

Referring to FIGS. 2 and 8, the threaded end 61 of the screw 60 passes through the central opening 18 of the top member 14 and the threaded pattern 62 threads into the threaded aperture 45 of the spinal fusion implant 40. The screw head 64 fits within the countersunk recess 19 of the top member 14 such that the screw head 64 is at or below the plane of the upper surface 20 of the top member 14. In the preferred embodiment, the central opening 18 has a diameter ranging from 4.5 mm to 5.5 mm, with 5.0 mm being the preferred diameter. The countersunk recess 19 has a diameter in the range of 6.0 mm to 8.0 mm with 7.0 mm being the preferred diameter.

Figure 15A:
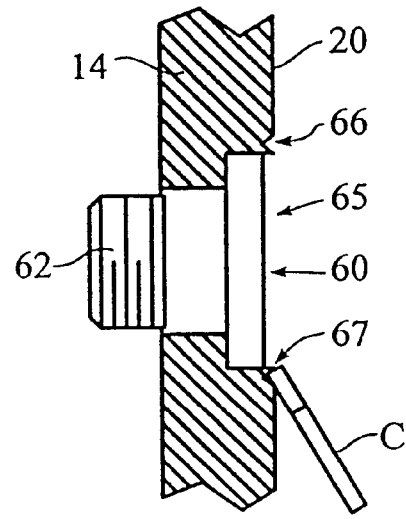
FIG. 15A is a cross sectional view of a securing means for locking the locking screw of the present invention.
Figure 15B:
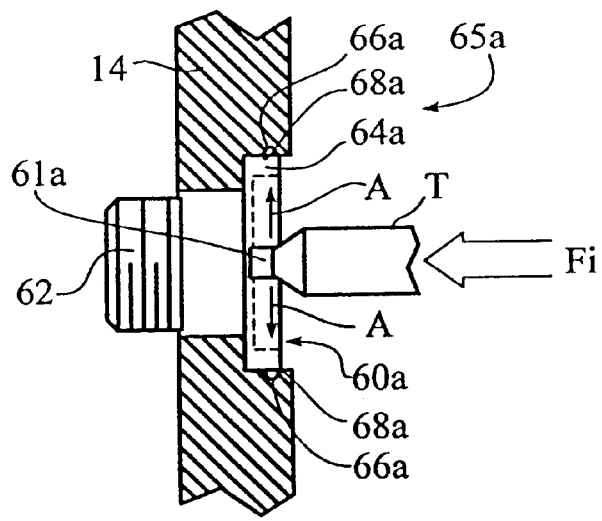
FIG. 15B is a cross sectional view of a first alternative embodiment of the securing means for locking the locking screw of the present invention.
Figure 15C:
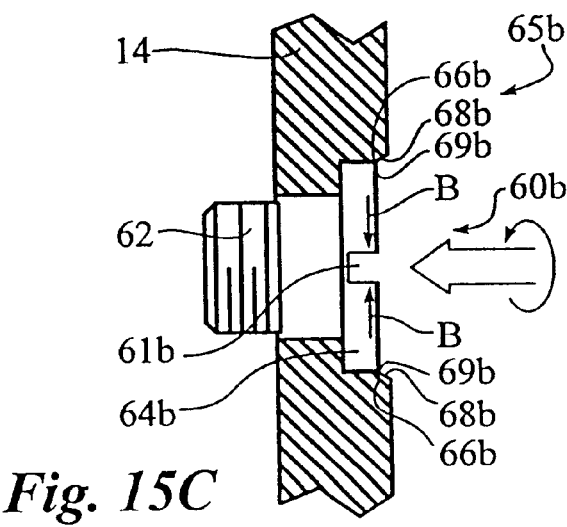
FIG. 15C is a cross sectional view of a second alternative embodiment of the securing means for locking the locking screw of the present invention.
Figure 19:
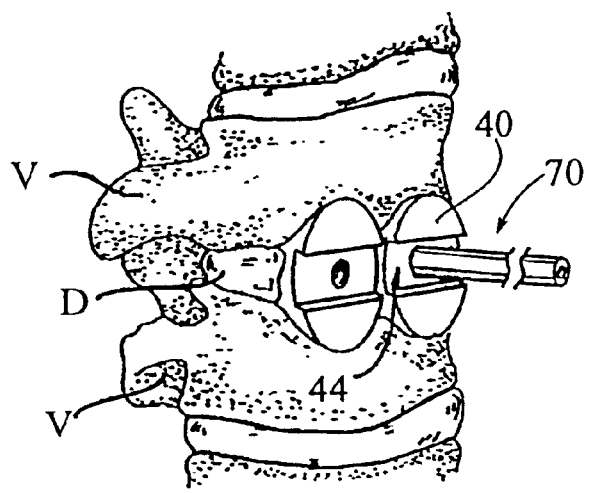
FIG. 19 is a perspective side view of the alignment rod attached to a spinal fusion implant inserted in the disc space between two adjacent vertebrae.

Referring to FIGS. 15A, 15B, and 15C, an enlarged cross sectional view of three different embodiments of a securing means 65 for locking the screw 60 once it is threaded to the spinal fusion implant 40 are shown. In FIG. 15A, the securing means 65 comprises a notch 66 in the surface 20 of the top member 14 which is preferably made of metal. Once the screw 60 is threaded and securely tightened to the spinal fusion implant 40, a chisel C is used to bend a portion 67 of the top member 14 into the central opening 18 and against the screw head 64 so as to prevent the outward excursion and any unwanted loosening of the screw 60.

In FIG. 15B, a second embodiment of the securing means 65a is shown comprising a central score 66a concentric with the central opening 18. A screw 60a having a slot 61a in the screw head 64a is threaded and securely tightened to the spinal fusion implant 40. An instrument T is partially inserted into slot 61a after which an impaction force $F_i$ is applied to the instrument T to spread apart the screw head 64a in the direction of the arrows A so that the screw head 64a becomes deformed from the impaction force $F_i$ and fits within the central score 66a. Once the screw head 64a is in the central score 66a, the outward excursion of the screw 60a is prevented by the top lip 68 of the central score 66a.

In FIG. 15C, a third embodiment of the securing means 65b is shown comprising a screw 60b having a screw head 64b with a slightly flanged portion 69b near the top and a slot 61b. The central opening 18 has along its circumference a recess 66b for receiving the flanged portion 69b of the screw head 64b. The securing means 65b relies on the natural resiliency of the metal screw head 64b such that when the screw 60b is being driven by a screw driver, the screw head 64b flexes in the direction of the arrows B. In this manner, the flanged portion 69b of the screw head 64b slides along the interior of the central opening 18 so that the screw head 64b is below the top lip 68b of the recess 66b. Once the screw driver is removed from the screw 60b, the screw head 64b returns to its natural state in the direction opposite to the arrows B so that the flanged portion 69b is within the recess 66b. The outward excursion of the screw 60 is thus prevented by the top lip 68b which blocks the screw head 64b by catching the flanged portion 69b.

FIGS. 16A–18 show the instrumentation used for installing the spinal fixation device 10. Referring to FIG. 16A, a driving instrument 80 used for inserting the spinal fixation device 10 into the vertebrae V is shown having a hollow tubular shaft 82 which terminates at one end to a bottom flat member 84 and terminates to a top flat member 86 at the other end. The bottom flat member 84 is preferably configured so that it conforms to the shape of the top member 14 of the staple member 12.

The driving instrument 80 has a pair of short posts 88a and 88b extending from the bottom flat member 84. The posts 88a and 88b are oriented on the bottom flat member 84 so as to correspond to the position of the openings 22a and 22b in the upper surface 20 of the top member 14 of the staple member 12. Each of the posts 88a and 88b fit into each of the openings 22a and 22b and keep the staple member 12 aligned on the bottom flat member 84 of the driving instrument 80. It is appreciated that the openings 22a and 22b in the top member 14 may be depressions within the surface 20 of the top member 14 or may be holes that pass through the top member 14. In the preferred embodiment, the openings 22a and 22b gave a diameter ranging from 1.5 mm to 3.5 mm, with 2.5 mm being the preferred diameter.

Referring to FIG. 16B, an alternative embodiment of the driving instrument 80' which is used for inserting into the vertebrae V the spinal fixation device 210, described in detail below in reference to FIG. 26, is shown having a hollow tubular shaft 82' which terminates at one end to a bottom flat member 84' and terminates to a top flat member 86' at the other end. The bottom flat member 84' is rectangular in shape so that it conforms to the shape of the top member 214 of the spinal fixation device 210.

The driving instrument 80' has a pair of short posts 88'a, 88'b, 88'c and 88'd extending from the bottom flat member 84'. The posts 88'a–88'd are oriented on the bottom flat member 84' so as to correspond to the position of the openings 222a–222d of the spinal fixation device 210. Each of the and keep the spinal fixation device 210 aligned on the bottom flat member 84' of the driving instrument 80'.

Referring to FIG. 17A, an alignment rod 70 comprising a cylindrical shaft 72 having a smooth exterior surface 73 and a threaded end 74 may be threadably attached to the threaded aperture 45 of the spinal fusion implant 40 is shown. The alignment rod 70 fits through the central opening 18 of the spinal fixation device 10 and is used to properly align the projections 16 and 17 on each side of the spinal fusion implant 40 prior to engaging the vertebrae V. Further, the alignment rod 70 also serves as a guide post for the drilling template instrument 50 described in greater detail below.

Referring to FIG. 17B, as an alternative embodiment of the alignment rod 70, a splined alignment rod 70' that has a finely splined surface 72' along its longitudinal axis and a threaded end 74' that may be attached to the threaded aperture 45 of the spinal fusion implant is shown.

Referring to FIG. 18, a drilling template instrument 50 for creating a pair of insertion holes 53a and 53b in each of the vertebrae V for receiving each of the projection 16 and 17 respectively is shown. The drilling template instrument 50 has a template 52 with a central aperture 54 therethrough and guide passages 55 and 56 for guiding a drill bit 51 of a drilling tool. Attached to the template 52 is a handle 58 which angles away from the template 52 so as not to obstruct the line of sight of the surgeon and to allow easy access to the template 52 and easy access to the guide holes 55 and 56 for the drill bit 51. Extending from the center of the bottom surface of the template 52 is a central member 59 (similar in structure and function to the central bar 35) for mating to an already implanted intervertebral spinal fusion implant 40. The central member 59 interdigitates with the depression 42 of the spinal fusion implant 40 so that the template 52 is properly oriented about the spinal fusion implant 40 and the guide holes 55 and 56 are properly oriented with respect to the vertebrae V adjacent to the spinal fusion implant 40. The alignment rod 70 serves as a guide post for the drill template instrument 50 as it fits through the central aperture 54 of the template 52 and aligns the template 52 with respect to the spinal fusion implant 40 and insures that it is coaxial. The central aperture 54 of the drilling template instrument 50 is smooth so that if it is placed over a splined alignment rod 70' the drilling template instrument 50 may be easily rotated about the splined alignment rod 70' into position such that the central member 59 is able to mate and interdigitate with the depression 44 of the spinal fusion implant 40.

Referring to FIGS. 19–24, the spinal fixation device 10 of the present invention is inserted in the following manner: At least one spinal fusion implant 40 is surgically implanted so that it is substantially within the disc space between two adjacent vertebrae V and engages at least a portion of each of the two adjacent vertebrae V. Once the spinal fusion implant 40 is in place, the alignment rod 70 is attached to the threaded aperture 45 of the spinal fusion implant 40. The alignment rod 70 serves as a guide post for the drilling template instrument 50 as it fits through the central aperture 54 of the template 52 and aligns the template 52 coaxially with respect to the spinal fusion implant 40.

Figure 20:
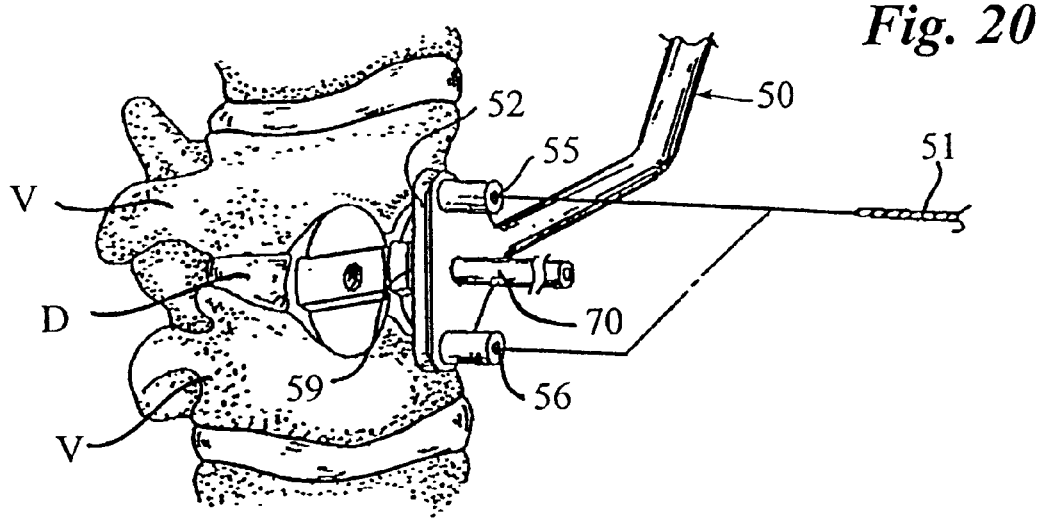
FIG. 20 illustrates the step of drilling guide holes in the vertebrae adjacent to the spinal fusion implant with the drill template instrument of FIG. 18.

Referring to FIG. 20, once the template 52 is properly aligned and the drilling template instrument 50 is seated so that the central member 59 interdigitates with the spinal fusion implant 40, the insertion holes 53a and 53b are drilled in each of the adjacent vertebrae V with a drilling instrument having a drill bit 51 with a diameter that is substantially smaller than the diameter of each the projections 16 and 17 of the staple member 12.

Once the drilling of the insertion holes 53a and 53b is completed, the drill template instrument 50 is removed from the spinal fusion implant 40 and from the alignment rod 70. The alignment rod 70 is left in place attached to the threaded aperture 45 of the spinal fusion implant 40.

Figure 21:
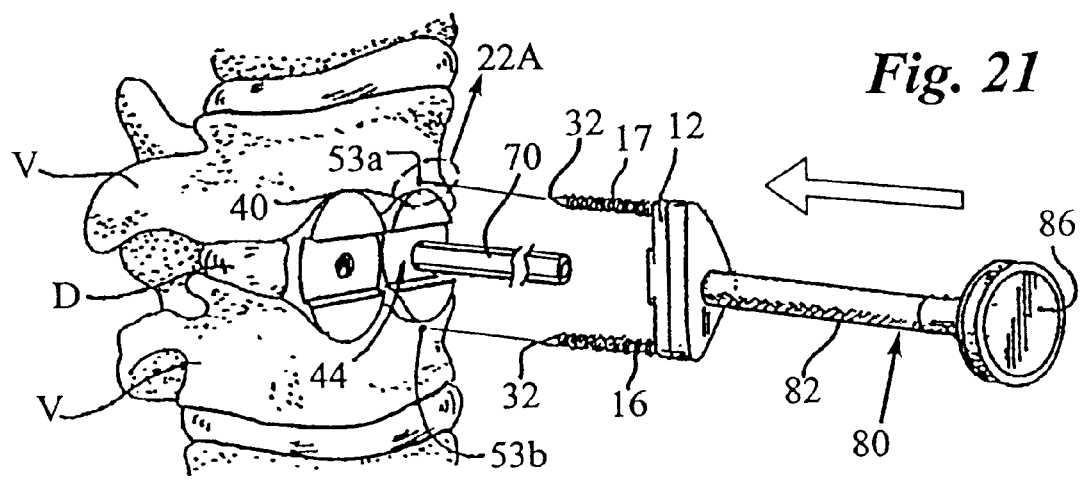
FIG. 21 illustrates a step of the method of inserting the spinal fixation device of the present invention with the alignment rod attached to the spinal fusion implant and the spinal fixation device placed on the driver instrumentation.

Referring to FIG. 21, the staple member 12 is placed onto the driving instrument 80 used for driving and fixing the staple member 12 into the vertebrae V so that the bottom flat member 84 and the posts 88a and 88b are aligned with the top member 14 and the depressions 22a and 22b of the top member 14. The alignment rod 70 serves as a guide post for the staple member 12 as it fits through the central opening 18 of the staple member 12 and aligns the staple member 12 coaxially with respect to the spinal fusion implant 40.

Figure 22:
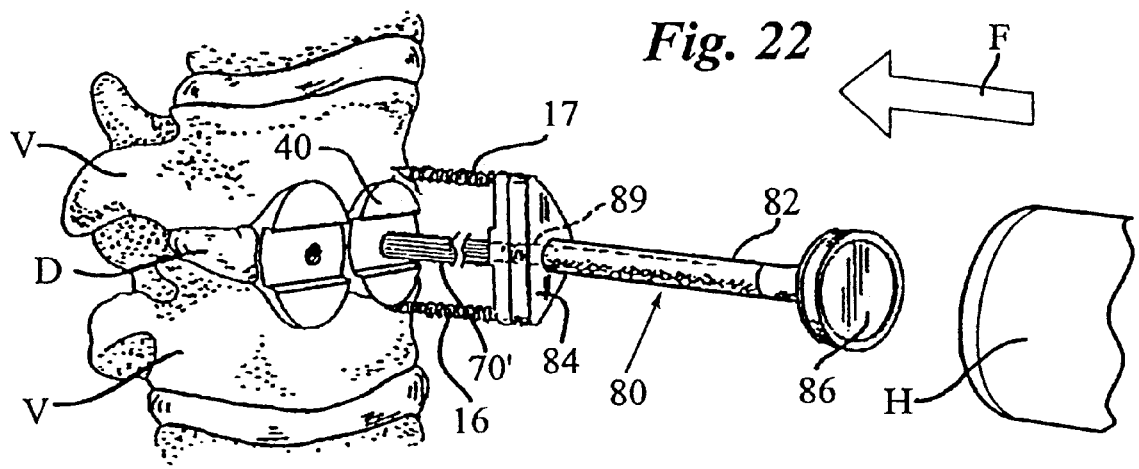
FIG. 22 illustrates a step of the short method of inserting the spinal fixation device of the present invention with the driver instrument engaging the splined alignment rod and a hammer for applying an impaction force and driving the driver instrument.
Figure 22A:
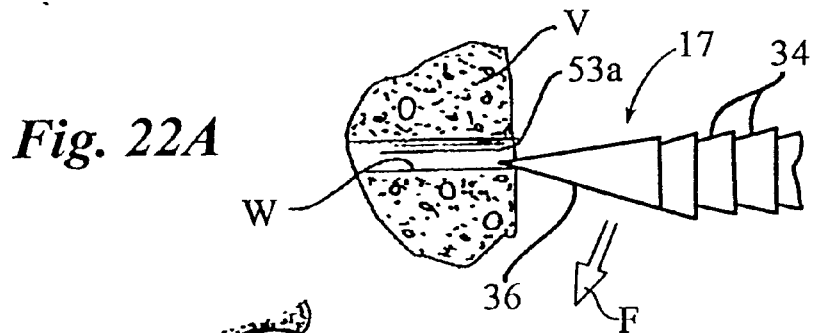
FIG. 22A is an enlarged fragmentary view of a projection being inserted into an insertion hole drilled within a vertebra shown in cross section taken along line 22A of FIG. 21.

Referring to FIG. 22, once the staple member 12 is properly placed onto the bottom flat member 84 of the driving instrument 80, the staple member 12 and the driving instrument 80 are aligned with respect to the alignment rod 70 so that the alignment rod 70 passes through the central opening 18 of the staple member 12 and is inserted into the central hollow portion 89 of the driving instrument 80. The staple member 12 and the driving instrument 80 are then lowered along the alignment rod 70 so that the sharp distal end 32 of each of the projections 16 and 17 comes into contact with the external surface of the vertebrae V and is aligned with the previously drilled insertion holes 53A and 53B As shown in FIG. 22A, it is preferred that the insertion holes 53a and 53b be drilled so that when the projections 16 and 17 are inserted into the holes 53a and 53b, the incline planed inner surface 36 of each of the projections 16 and 17 contacts the inner wall W of the insertion holes 53a and 53b that is closest to the spinal fusion implant 40. In this manner a compression force F is created as each of the projections 16 and 17 of the staple member 12 is inserted into insertion holes 53a and 53b, respectively, compressing the bone of the vertebrae V toward the spinal fusion implant 40.

Figure 23:
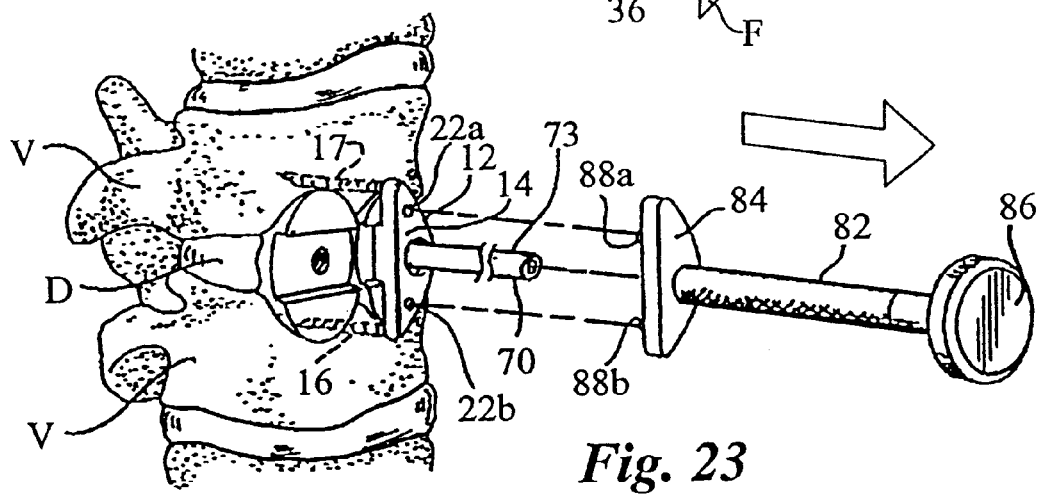
FIG. 23 illustrates another step of the method of inserting the spinal fixation device of the present invention in which the spinal fixation device has been driven into the vertebrae and the driver instrumentation has been removed.

Referring to FIG. 23, the staple member 12 is then driven into the vertebrae V by applying a high impaction force to the driving instrument 80 with a hammer H or other impacting means against the top flat member 86 of the driving instrument 80. The staple member 12 is driven into the vertebrae V such that the projections 16 and 17 are moved forward into the insertion holes 53a and 53b, respectively, until the bottom surface 30 of the top member 14 of the staple member 12 comes to rest against the surface of the vertebrae V.

Figure 24:
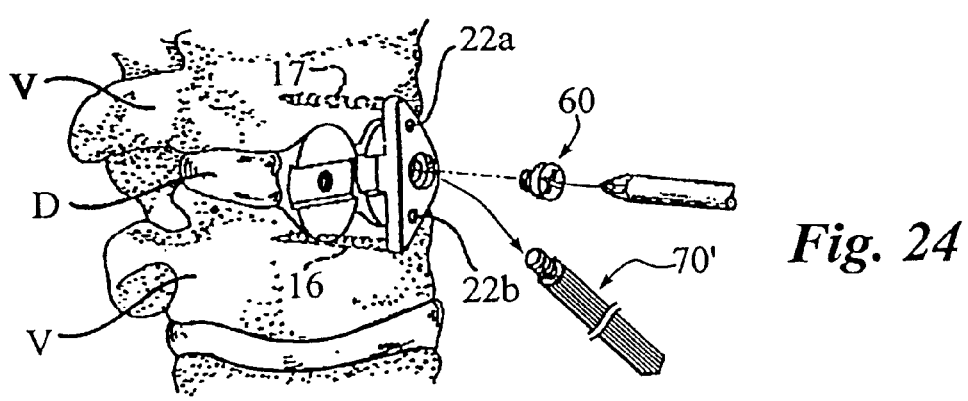
FIG. 24 illustrates another step of the method of inserting the spinal fixation device of the present invention with the splined alignment rod being removed from the spinal fusion implant and the locking screw being inserted and secured the spinal fixation device to the spinal fusion implant.

Referring to FIGS. 23–24, the driving instrument 80 is lifted away from the alignment rod 70 so that the alignment rod 70 is no longer within the central hollow portion 89 of the driving instrument 80. The alignment rod 70 is unthreaded from the threaded aperture 45 and is removed from the spinal fusion implant 40. The staple member 12 is secured to the spinal fusion implant 40 with the locking screw 60 which has a threaded pattern 62 with a reduced pitch. The reduced pitch of the locking screw 60 locks the locking screw 60 to the spinal fusion implant 40 with minimal turning of the locking screw 60 and prevents any unwanted loosening. Further, any of the three embodiments of the securing means 65, 65a or 65b described above in reference to FIGS. 15A–15C may be used to further prevent any unwanted loosening and outward excursion of the screw 60.

Referring back to FIG. 12, once the staple member 12 is driven into the vertebrae V and is secured to the spinal fusion implant 40, the spinal fusion implant 40 is prevented from rotating along its rotational axis R by its connection to the staple member 12 which is fixated across the disc space between the vertebrae V. The staple member 12 is prevented from backing out from the vertebrae V along the longitudinal axis L by its connection to the spinal fusion implant 40 and by the segmented and ratcheted portions 34 of the projections 16 and 17. In this manner, the staple member 12 and the spinal fusion implant 40 interact to prevent the dislodgement of each other from the vertebrae V in which they are implanted. Thus, the staple member 12 is made safe against dislodgement by attachment to the spinal fusion implant 40 and the stability of the spinal fusion implant 40 is assured as it is also stabilized by the staple member 12 and each works in connection with the other to remove the only remaining degree of freedom that would allow for the disengagement of either. In addition, the incline planed inner surface 36 at the distal end 32 of the projections 16 and 17 forces bone toward the spinal fusion implant 40 along force lines F to further secure the spinal fusion implant 40 and further prevent the dislodgement of the spinal fusion implant 40.

It is appreciated by those skilled in the art that when the bone of the vertebrae V is sufficiently soft, a shorter method (hereinafter referred to as the "Short Method") of inserting the spinal fixation device 10 is possible by omitting the steps of drilling the insertion holes 53a and 53b prior to inserting the staple member 12 into the vertebrae V.

Referring to FIG. 22, in the Short Method, the splined alignment rod 70' that is finely splined along its longitudinal axis is used instead of the alignment rod 70. Once the splined alignment rod 70' has been attached to the spinal fusion implant 40, the staple member 12 may be placed over the splined alignment rod 70' so that the splined alignment rod 70' passes through the aperture 18 and into the central aperture 89 of the driving instrument 80. The central aperture 89 of the driving instrument 80 is correspondingly splined to the splines of the splined alignment rod 70' so that the staple member 12 can be aligned with respect to the spinal implant 40. The alignment of the staple member 12 and the driving instrument 80 is maintained as the corresponding splines of the central aperture 89 interdigitate with the splines of the splined alignment rod 70' and prevent the rotation of the staple member 12 about the splined alignment rod 70'. The prevention of rotation about the splined alignment rod 70'is especially important when the Short Method is used to insert the spinal fixation device 10, as no insertion holes 53a and 53b have been drilled in the vertebrae V. The staple 12 can be driven directly into the vertebrae V by the application of a high impaction force to the driving instrument 80 as described above and shown in FIG. 22.

Once the staple member 12 is driven into the vertebrae V, the steps of the longer method described above are used to secure the spinal fixation device to the spinal fusion implant 40 are the same. The Short Method of inserting the staple member 12 reduces the amount of time required to insert and secure the spinal fixation device 10 of the present invention and thus reduces the overall duration of the spinal fixation surgical procedure.

While the present invention has been described with respect to its preferred embodiment, it is recognized that alternative embodiments of the present invention may be devised without departing from the inventive concept.

For example, referring to FIG. 25, a first alternative embodiment of a spinal fixation device 110 having a staple member 112 with a top member 114 generally in the shape of an elongated oval having two curved sides 124a and 124b is shown. In this alternative embodiment, the curved sides 124a and 124b have upper edges 125a and 125b, respectively, that are radiused to conform to the external curvature of the vertebrae V thereby creating smooth contoured surfaces as described above for the spinal fixation device 10, the preferred embodiment of the present invention. The top member 114 has openings 122a and 122b in the upper surface 120 of the top member 114 and has two projections 116 and 117 depending downwardly from the bottom surface 130 of the top member 114 at opposite ends of the staple member 112. The projections 116 and 117 are the same as the projections 16 described above for the preferred embodiment.

Referring to FIG. 26, a second alternative embodiment of the spinal fixation device 210 having a staple member 212 is shown with a top member 214 that is generally rectangular in shape and has an upper surface 220 with openings 222a, 222b, 222c, and 222d. The top member 214 has four projections 216, 217, 218, and 219 depending from its bottom surface at each of its corners. The projections 216–217 are the same as the projections 16 and 17 described above in the preferred embodiment. The top member 214 has four straight sides 228a, 228b, 228c, and 228d having upper edges 225a, 225b, 225c, and 225d, respectively, that are radiused to conform to the to external curvature of the vertebrae V create a smooth surface as described above for the preferred embodiment. The driving instrument 80' shown in FIG. 16B is used to insert the spinal fixation device 210.

Referring to FIG. 27, a third alternative embodiment of the spinal fixation device 310 having a staple 312 with a top member 314 that is generally triangular is shown. The top member 314 has two projections 316 and 317 depending from the bottom surface of the top member 314 that engage the vertebrae V. Extending from the center of the bottom surface of the top member 314 is a central member 390 which is similar to the central bar 35 of the preferred embodiment of the spinal fixation device 10 in that the central member 390 interdigitates with the depression 44 of the spinal fusion implant 40. However, the central bar 390 also has an extension arm 392 that extends laterally from the top member 314 to span the diameter of an adjacent spinal fusion implant 41. The extension arm 392 interdigitates with the depression 44 of the spinal implant 41. The extension arm 392 has a central aperture 394 for receiving a screw 60b used to couple the extension arm 392 to the spinal fusion implant 41. In this manner, a single spinal fixation device 310 is capable of interdigitate with two adjacent spinal fusion implants 40 and 41 to lock and prevent the rotation and any excursion of the spinal fusion implants 40 and 41. The fixation of two spinal fusion implants 40 and 41 is possible while leaving no protruding metal, such as the top member 314, on the side of the spine where the vessels are located in close approximation to the vertebrae as is the case with the $L_4$ and $L_5$ vertebrae where the vessels are located over the left side of those vertebrae. It is appreciated that any of the securing means 65–65b, described above may be used to lock the screw 60b to the extension arm 392.

Referring to FIG. 28, a fourth alternative embodiment of the spinal fixation device 410 having a staple member 412 with a top member 414 that is generally triangular in shape is shown in the installed position. The top member 414 is wider and larger than top member 14 as it is used with an implant 440 having a large diameter in the range of 22.0 mm to 28.0 mm. The top member 414 needs to be wider when used with implant 440 in order to provide a central bar 435 of sufficient length to interdigitate and mate with the preferred embodiment of the present invention for use with a multi-segmental spinal alignment means 600 described in greater detail below in that the staple 512 provides a more solid anchoring means that can resist greater torsion forces resulting from the application of the multi-segmental spinal alignment means 600 to align the spine.

Alternatively, for all of the embodiments described above, the spinal fixation device 10 of the present invention could be made of resorbable materials, such as bio-compatible resorbable plastics, that resorb at an appropriate rate such that once the spinal fixation device 10 is no longer needed (i.e. when spinal fusion is complete) the body would resorb the spinal fixation device 10. One such resorbable material is polygalactone, however any other resorbable plastic or other material safely usable within the human body are also within the scope of the present invention.

Further, the spinal fixation device could be only in part resorbable such that the projections 16 and 17 of the staple member 12 would be non-resorbable and would remain incarcerated in the vertebrae V and sealed off once the resorbable portion of the staple is resorbed by the body.

Referring to FIGS. 33 and 34, as a further application, the spinal fixation device 510 of the present invention may be used as an anchor for a multi-segmental spinal alignment means 600, such that a multiplicity of spinal fixation devices may then be interconnected via a cable, rod, bar, or plate, so as to achieve or maintain any desired multi-segment spinal alignment. In the preferred embodiment, the multi-segmental spinal alignment means 600 comprises more than one spinal fixation device 510 of the present invention placed in series along the spine such that each spinal fixation device 510 spans one disc D and engages two adjacent vertebrae V. The spinal fixation device 510 is preferred over the other embodiments of the present invention in that it has a greater area of engagement with the vertebrae V so as to provide a solid anchoring means for the multi-segmental spinal alignment means 600. However, it is appreciated that other embodiments including but not limited to those described herein may be utilized as anchoring means for the multi-segmental spinal alignment means 600

When used as an anchor, each spinal fixation device 510 interdigitates with and is connected to a spinal fusion implant 610 having an insertion end 612, an interior chamber 614 and is inserted in the disc space between the two adjacent vertebrae. The spinal fusion implant 610 has a threaded blind hole 620 for receiving a threaded post 622 therein. The blind hole 620 has a casing that is made of strong surgically, implantable material such as, but not limited to titanium. The casing 624 extends from the insertion end 612 of the spinal fusion implant 610 into the interior central chamber 614. The insertion end 612 has a rigid construction that is capable of withstanding high torsion forces resulting from the tensioning of the multi-segmental spinal alignment means to align segments of the spine. In the preferred embodiment, the insertion end 612 of the spinal fusion implant has an end portion 626 that closes the insertion end 612. The end portion is substantially thicker than the rest of the spinal fusion implant 610 and in the preferred embodiment, the end portion 626 has thickness ranging from 1.5 mm to 4.0 mm, with 2.5 mm being the preferred thickness.

Referring to FIG. 34, the threaded post 622 has a threaded end 628 with a locking thread pattern that is substantially longer than the locking thread pattern 62 of the screw 60 described above and a head portion 630 having a hole 632 for receiving a rod 634 or a cable therethrough. The head portion 630 has a rounded exterior surface to prevent any damage such as aortic erosion to the vessels in the area adjacent to the spine. In the preferred embodiment the threaded post has a diameter ranging from 3.0 mm to 6.0 mm, with 4.5 mm being the preferred diameter and has a length ranging from 15.0 mm to 25.0 mm, with 20.0 mm being the preferred length. The head portion 630 extends at a height above the top member 514 of the spinal fixation device 510 of approximately 8.0 mm to 16.0 mm, with 12.0 being the height preferred once it is threadably attached to the spinal fusion implant 610 such that it does not significantly protrude from the spinal column into the tissue and vessels adjacent thereto.

Once the threaded post 622 is attached to the spinal fusion implant 610, the head portion 630 of each threaded post 622 are connected to one another by the rod 634 having a sufficient diameter to fit through the hole 632 of each head portion 630. The rod 634 has at least a portion thereof that is threaded so that a plurality of lock nuts 638 may be used to secure the rod 634 to the head portions 630. The lock nuts 638 may also be used as length adjusting means to adjust the length of the rod 634 between head portions 630 so that segmental portions of the spine may be held closer together or held further aport for the purposes of aligning the spine. It is appreciated that a plurality of multi-segmental spinal alignment means 600 may be placed in series either on one side or on opposite sides of the spine, such that one side of the spine may be extended while the other side may be held stationary or may be compressed in order to achieve proper spinal alignment. The multi-segment spinal alignment may be maintained by keeping the rod tensioned with the lock nuts 638 or by any other means well known by those skilled in the art. It is also appreciated that in place of a rod 634 a cable, a plate or any other means well known by those skilled in the art may be used to interconnect the multi-segmental spinal alignment means.

Referring to FIG. 35, a sixth alternative embodiment of the spinal fixation device of the present invention is shown and generally referred to by the numeral 710. The spinal fixation device 710 comprises a top member 714 that is similar to the top member 14 described above, except that it does not have projections 16 and 17 extending from the bottom surface. Like numbers are being used to designate identical features of the top members 14 and 714.

In the top member 714, instead of having projections 16 and 17, independent projection members 716 and 717 in the form of screws are used to secure the top member 714 of the spinal fixation device 710 to the vertebrae V of the spine. The projection screw members 716 and 717 each terminate in a sharp distal end 720 and 722 respectively, have a threaded portion 723, and have screw heads 724 and 726 for engaging a screw driver or similar driving instrument.

The top member 714 has a hole 728 on one end and a hole 730 at its other end through which each of the projection screw members 716 and 717 respectively, may pass. The projections screw members 716 and 717 pass through the holes 728 and 730 to engage the vertebrae V. Each of the holes 728 and 730 has a concentric counter sunk recess 732 and 734 for receiving and seating the screw heads 724 and 726 of the projection screw members 716 and 717 so that the screw heads 724 and 726 are flush or below the top surface 20 of the top member 714 once inserted into the vertebrae V.

As the projection screw members 716 and 717 are threaded, they can be rotationally advanced into the vertebrae instead of by way of an impaction force such that the potential for damage to the vertebrae V is reduced. The threads of the threaded portion 723 follow one another as the projection screw members 716 and 717 are being screwed into the bone such that the integrity of the vertebrae V is preserved. Also, as the projection screw members 716 and 717 are independent from the top member 714, the penetration depth of the spinal fixation device 710 into the bone of the vertebrae V may be easily altered by selecting different sized projection screw members 716 and 717 appropriate for the particular vertebrae being fused. Further, it is possible to configure the holes 728 and 730 in the top member 714 such that the projection screw members 716 and 717 may be inserted into the vertebrae V from a number of different angles relative to the top member 714.

Adjacent and proximate to each of the holes 728 and 730 are threaded openings 740 and 742, respectively, for receiving locking screws 744 and 746 respectively. Each of the locking screws 744 and 746 have a head portion 750 and 752 and a locking thread portion 754 and 756 for threadably and lockably engaging the threaded openings 740 and 742. The locking screws 744 and 746 are attached to the top member 714 after the projection screw members 716 and 717 have been inserted into the vertebrae V. At least a part of the head portion 750 and 752 blocks and preferably makes contact with the screw projections 716 and 717 to prevent any unwanted loosening and outward excursion of the screw projections 716 and 717.

It is appreciated that the projection members 716 and 717, instead of being threaded screws, may have a number of other configurations such as, but not limited to, the configurations of the projections described above for the various embodiments of the present invention. If the projections members 716 and 717 are ratcheted instead of being threaded, they can be driven into the vertebrae V with a driving instrument and impaction force as described above for the method of the present invention.

While the present invention has been described with respect to its preferred embodiment and a number of alternative embodiments, it is recognized that additional variations of the present invention may be devised without departing from the inventive concept and scope of the present invention.

What is claimed is:

1. A multi-segmental spinal alignment apparatus for linking segments of the spine, comprising:
    a first spinal implant adapted to be surgically implanted at least in part within a first disc space between two adjacent vertebrae in a segment of the spine, said first spinal implant being adapted to contact both of the vertebrae adjacent to the first disc space when the disc space has been restored to approximate a normal height for the disc space, said first spinal implant having an end configured to receive a connector;
    a second spinal implant adapted to be surgically implanted at least in part within a second disc space between two adjacent vertebrae in another segment of the spine, said second spinal implant being adapted to contact both of the vertebrae adjacent to the second disc space when the disc space has been restored to approximate a normal height for the disc space; and
    a connector attached to said first and second spinal implants for connecting said first and second spinal implants.

2. The apparatus of claim 1, wherein said second spinal implant has an end portion configured to receive said connector.

3. The apparatus of claim 2, wherein each of said end portions has an aperture for receiving said connector.

4. The apparatus of claim 3, wherein said apertures are generally aligned along the longitudinal axis of the spine.

5. The apparatus of claim 1, wherein each of said end portions are detachable.

6. The apparatus of claim 1, wherein each of said end portions is a coupler.

7. The apparatus of claim 6, wherein each of said couplers are detachable.

8. The apparatus of claim 6, wherein each of said couplers includes an aperture generally along the longitudinal axis of the spine for receiving said connector.

9. The apparatus of claim 6, wherein each of said couplers has a head and a shank, said head having an aperture for receiving the connector.

10. The apparatus of claim 9, wherein each of said first and second implants has an aperture for receiving said shanks.

11. The apparatus of claim 10, wherein said shanks and said apertures have cooperating threads.

12. The apparatus of claim 1, wherein said first and second implants include upper and lower portions with at least one opening in each of said upper and lower portions for permitting bone growth from one of the adjacent vertebrae through said spinal implant to the other of the adjacent vertebrae.

13. The apparatus of claim 12, further comprising a hollow interior within each of said first and second implants for holding bone growth promoting material, said hollow interior being in communication with at least one opening in each of said upper an lower portions.

14. The apparatus of claim 1, wherein said first and second implants include upper and lower portions that are arcuate.

15. The apparatus of claim 1, wherein said first and second implants further comprise a protrusion for engaging the adjacent vertebrae.

16. The apparatus of claim 15, wherein said protrusion is a thread.

17. The apparatus of claim 1, wherein said connector is selected from one of a rod, a cable, a plate, and a bar.

18. The apparatus of claim 1, further comprising means for adjusting the length of said connector between said first and second spinal implants for aligning segments of the spine.

19. The apparatus of claim 18, wherein said length adjusting means includes a threaded member on said connector for varying the length of said connector between said first and second spinal implants.

20. The apparatus of claim 18 further comprising a means for locking said length adjusting means at a selected length.

21. The apparatus of claim 1, further comprising a third spinal implant adapted to be surgically implanted in the first disc space, a fourth spinal implant adapted to be surgically implanted in the second disc space, and a second connector attached to both of said third and fourth implants.

22. The apparatus of claim 21, wherein said first and second connectors are adapted to be placed on one side of the spine.

23. The apparatus of claim 21, wherein said first and second connectors are adapted to be placed on opposite sides of the spine.

24. The apparatus of claim 21, wherein said first and second connectors are selected from one of a rod, a cable, a plate, and a bar.

25. The apparatus of claim 1, wherein said first and second spinal implants include an artificial material other than bone.

26. The apparatus of claim 1, wherein said implants are configured for implantation across a disc space in the thoracolumbar region of the human spine.

27. A multi-segmental spinal alignment apparatus for linking multiple implants surgically implanted in the human spine, comprising:
    a first spinal implant adapted to be surgically implanted within a first location of the spine;
    a second spinal implant adapted to be surgically implanted within a second location of the spine, each of said first and second spinal implants having opposed arcuate portions over at least a portion of their length and at least one opening in each of said opposed arcuate portions along the length of said implants for permitting growth of bone into and through said implants, said implants having a hollow interior for holding bone growth promoting material, said hollow interior of each of said implants being in communication with at least one opening in each of said opposed arcuate portions; and a protrusion extending from the exterior of each of said implants for engaging bone in the spine; and a connector having a width and a length, said connector being attached along its length to each of said implants for connecting said implants together, each of said implants having a width greater than said width of said connector measured transverse to the longitudinal axis of the spine.

28. The apparatus of claim 27, wherein at least one of said insertion and trailing ends are open for loading bone growth promoting materials into said hollow interior.

29. The apparatus of claim 28, further comprising an end cap for closing said open end.

30. The apparatus of claim 27, wherein each of said implants has an end portion configured to receive said connector.

31. The apparatus of claim 27, wherein each of said implants has an end portion configured to couple to said connector.

32. The apparatus of claim 31, wherein each of said end portions has an aperture for receiving said connector.

33. The apparatus of claim 31, wherein said apertures are generally aligned along the longitudinal axis of the spine.

34. The apparatus of claim 27, wherein each of said end portions is detachable.

35. The apparatus of claim 27, wherein each of said end portions is a coupler.

36. The apparatus of claim 35, wherein each of said couplers is detachable.

37. The apparatus of claim 35, wherein each of said couplers include an aperture generally along the longitudinal axis of the spine for receiving said connector.

38. The apparatus of claim 35, wherein each of said couplers have a head and a shank, said head having an opening for receiving the connector.

39. The apparatus of claim 38, wherein each of said implants has an aperture for receiving said shank.

40. The apparatus of claim 39, wherein said shank and said apertures have cooperating threads.

41. The apparatus of claim 27, wherein said protrusion of said opposed arcuate portions is a thread.

42. The apparatus of claim 27, wherein said connector is selected from one of a rod, a cable, a plate, and a bar.

43. The apparatus of claim 27, further comprising means for adjusting the length of said connector between said implants for aligning segments of the spine.

44. The apparatus of claim 43, wherein said length adjusting means includes a threaded member on said connector for varying the length of said connector between said implants.

45. The apparatus of claim 43, further comprising means for locking said length adjusting means at a selected length.

46. The apparatus of claim 27, further comprising a third spinal implant adapted to be surgically implanted in a third location in the spine, a fourth spinal implant adapted to be surgically implanted in a fourth location in the spine, and a second connector attached to both of said third and fourth implants.

47. The apparatus of claim 46, wherein said first and second connectors are adapted to be placed on one side of the spine.

48. The apparatus of claim 46, wherein said first and second connectors are adapted to be placed on opposite sides of the spine.

49. The apparatus of claim 46, wherein said second connector is selected from one of a rod, a cable, a plate, and a bar.

50. The apparatus of claim 27, wherein said implants include an artificial material other than bone.

51. A multi-segmental spinal alignment apparatus for linking segments of the spine, comprising:

a first spinal implant adapted to be surgically implanted at least in part within a first disc space between two adjacent vertebrae in a segment of the spine, said first spinal implant being adapted to contact both of the vertebrae adjacent to the first disc space when the disc space has been restored to approximate a normal height of the disc space;

a second spinal implant adapted to be surgically implanted at least in part within a second disc space between two adjacent vertebrae in another segment of the spine, said second spinal implant being adapted to contact both of the vertebrae adjacent to the second disc space when the disc space has been restored to approximate a normal height of the disc space;

a connector having a length sufficient to span the distance from said first disc space to said second disc space to connect said implants; and a plurality of couplers for coupling said connector to each of said spinal implants.

52. The apparatus of claim 51, wherein each of said spinal implants has an end portion configured to receive said at least one of said couplers.

53. The apparatus of claim 51, wherein each of said implants has an end portion configured to couple to said at least one of said couplers.

54. The apparatus of claim 52, wherein each of said couplers has an aperture for receiving said connector.

55. The apparatus of claim 54, wherein said apertures are generally aligned along the longitudinal axis of the spine.

56. The apparatus of claim 52, wherein each of said couplers is detachable.

57. The apparatus of claim 52, wherein each of said couplers has a head and a shank, said head having an opening for receiving the connector.

58. The apparatus of claim 57, wherein each of said implants have an aperture for receiving said shank.

59. The apparatus of claim 58, wherein each of said shanks and each of said apertures has cooperating threads.

60. The apparatus of claim 51, wherein said implants include upper and lower portions with a plurality of openings for permitting bone growth from one of the adjacent vertebrae through each of said implants to the other of the adjacent vertebra.

61. The apparatus of claim 60, further comprising a hollow interior for holding bone growth promoting material, said hollow interior within each of said implants being in communication with at least two of said plurality of openings.

62. The apparatus of claim 51, wherein said implants include upper and lower portions that are arcuate.

63. The apparatus of claim 51, wherein said implants further comprise a protrusion for engaging the adjacent vertebrae.

64. The apparatus of claim 63, wherein said protrusion of said implants is a thread.

65. The apparatus of claim 51, wherein said connector is selected from one of a rod, a cable, a plate, and a bar.

66. The apparatus of claim 51, further comprising means for adjusting the length of said connector between said implants for aligning segments of the spine.

67. The apparatus of claim 66, wherein said length adjusting means includes a threaded member on said connector for varying the length of said connector between said implants.

68. The apparatus of claim 66, including means for locking said length adjusting means at a selected length.

69. The apparatus of claim 51, further comprising a third spinal implant adapted to be surgically implanted in the first disc space, a fourth spinal implant adapted to be surgically implanted in the second disc space, and a second connector having a length sufficient to span the distance between said first and second disc spaces to connect said third and fourth spinal implants.

70. The apparatus of claim 69, wherein said first and second connectors are adapted to be placed on one side of the spine.

71. The apparatus of claim 69, wherein said first and second connectors are adapted to be placed on opposite sides of the spine.

72. The apparatus of claim 69, wherein said first and second connectors are selected from one of a rod, a cable, a plate, and a bar.

73. The apparatus of claim 51, wherein said implants include an artificial material other than bone.

74. The apparatus of claim 51, wherein said implants are configured for implantation across a disc space in the thoracolumbar region of the human spine.

75. A method for linking multiple segments of a human spine, comprising the steps of:
 implanting a first spinal implant adapted to be surgically implanted at least in part within a first disc space between two adjacent vertebrae in a segment of the spine, said first spinal implant being adapted to contact both of the vertebrae adjacent to the first disc space when the disc space has been restored to approximate a normal height for the disc space, said first spinal implant having a trailing end configured to receive a connector;
 implanting a second spinal implant adapted to be surgically implanted at least in part within a second disc space between two adjacent vertebrae in a segment of the spine, said second spinal implant being adapted to contact both of the vertebrae adjacent to the second disc space, when the disc space has been restored to approximate a normal height for the disc space; and
 attaching a connector to both of said first and second spinal implants.

76. The method of claim 75, further comprising the step of positioning said implants in spatial relationship to each other.

77. The method of claim 75, wherein the step of implanting said second implant includes implanting said second implant having a trailing end configured to receive a connector.

78. The method of claim 76, wherein the positioning step includes the sub-step of varying the length of the connector between said implants.

79. The method of claim 76, wherein the positioning step includes the sub-step of aligning segments of the spine.

80. The method of claim 76, further comprising the step of locking said implants in a fixed spatial relationship to each other.

81. The method of claim 75, further comprising the steps of implanting a third spinal implant in the first disc space and implanting a fourth spinal implant in the second disc space.

82. The method of claim 81, wherein the attaching step includes attaching a second connector to both of said third and fourth spinal implants.

83. The method of claim 81, further comprising the step of positioning on the same side of the spine first and second connectors for connecting spinal implants.

84. The method of claim 81, further comprising the step of positioning on opposite sides of the spine first and second connectors for connecting spinal implants.

85. The method of claim 75, further comprising the step of tensioning said connector between said implants.

86. The method of claim 75, wherein the attaching step includes the sub-step of connecting at least three spinal implants in a series along segments of the spine.

87. The method of claim 75, wherein the implanting steps include implanting said spinal implants including an artificial material other than bone.

88. The method of claim 75, wherein the implanting steps include implanting said implants across a disc space in the thoracolumbar region of the human spine.

89. A method for linking multiple segments of the spine, comprising the steps of:
 implanting a first spinal implant adapted to be surgically implanted in a first location of the spine, said first spinal implant having a maximum width and opposed arcuate portions over at least a portion of its length and a plurality of openings along the length of said implant passing therethrough for permitting growth of bone into said first implant, said first implant having a hollow interior for holding bone growth promoting material, said hollow interior being in communication with at least two of said plurality of openings, and a protrusion extending from the exterior of said first implant for engaging bone in the spine;
 implanting a second spinal implant adapted to be surgically implanted in a second location in the spine, said second implant having a maximum width and opposed arcuate portions over at least a portion of its length and a plurality of openings along the length of said second implant passing therethrough for permitting growth of bone into said second implant, said second implant having a hollow interior for holding bone growth promoting material, said hollow interior being in communication with at least two of said plurality of openings, and a protrusion extending from the exterior of said second implant for engaging bone in the spine; and
 aligning a connector to both of said implants, said connector having a width measured transverse to the longitudinal axis of the spine less than the maximum width of each of said implants.

90. The method of claim 89, wherein the implanting steps include the sub-step of implanting said implants having at least one of said insertion and trailing ends open for loading bone growth promoting materials into said hollow interior.

91. The method of claim 90, further comprising the step of providing an end cap for closing said open end.

92. The method of claim 89, further comprising the step of positioning said implants in spatial relationship to each other.

93. The method of claim 92, wherein the positioning step includes the sub-step of varying the length of the connector between said implants.

94. The method of claim 92, wherein the positioning step includes the sub-step of aligning segments of the spine.

95. The method of claim 92, further comprising the step of locking said implants in a fixed spatial relationship to each other.

96. The method of claim 89, further comprising the steps of implanting a third spinal implant at a third location in the spine and implanting a fourth spinal implant at a fourth location in the spine.

97. The method of claim 96, wherein the attaching step includes attaching a second connector to both of said third and fourth spinal implants.

98. The method of claim 96, further comprising the step of positioning on the same side of the spine first and second connectors for connecting spinal implants.

99. The method of claim 96, further comprising the step of positioning on opposite sides of the spine first and second connectors for connecting implants.

100. The method of claim 89, further comprising the step of tensioning said connector between said implants.

101. The method of claim 89, wherein the attaching step includes the sub-step of connecting at least three spinal implants in a series along segments of the spine.

102. The method of claim 89, wherein the implanting steps include implanting said spinal implants including an artificial material other than bone.

103. An apparatus for linking multiple spinal implants, comprising:

a first spinal implant adapted to be surgically implanted at least in part within a disc space between two adjacent vertebrae in a segment of the spine, said first spinal implant being adapted to contact both of the vertebrae adjacent to the disc space;

a second spinal implant adapted to be surgically implanted at least in part within the same disc space in which said first spinal implant is to be implanted, said second spinal implant being adapted to contact both of the vertebrae adjacent to the disc space; and a connector attached to said first and second spinal implants for connecting said first and second spinal implants.

104. The apparatus of claim 103, wherein each of said implants has an end portion configured to couple to said connector.

105. The apparatus of claim 104, wherein each of said implants has an end portion configured to receive said connector.

106. The apparatus of claim 104, wherein each of said end portions has an opening for receiving said connector.

107. The apparatus of claim 104, wherein said end portions are detachable.

108. The apparatus of claim 104, wherein each of said end portions is a coupler.

109. The apparatus of claim 108, wherein each of said couplers are detachable.

110. The apparatus of claim 108, wherein each of said couplers has a head and a shank, said head having an opening for receiving the connector.

111. The apparatus of claim 110, wherein each of said implants has an aperture for receiving said shank.

112. The apparatus of claim 111, wherein said shanks and said apertures have cooperating threads.

113. The apparatus of claim 103, wherein said implants include upper and lower portions with a plurality of openings for permitting bone growth from one of the adjacent vertebrae through each of said implants to the other of the adjacent vertebrae.

114. The apparatus of claim 113, further comprising a hollow interior within each of said implants for holding bone growth promoting material, said hollow interior being in communication with at least two of said plurality of openings.

115. The apparatus of claim 103, wherein said implants have upper and lower portions that are arcuate.

116. The apparatus of claim 103, wherein said implants further comprise a protrusion for engaging the adjacent vertebrae.

117. The apparatus of claim 116, wherein said protrusion of said upper and lower portions of said implants is a thread.

118. The apparatus of claim 103, wherein said connector is selected from one of a rod, a cable, a plate, and a bar.

119. The apparatus of claim 103, wherein said implants include artificial material other than bone.

120. The apparatus of claim 103, wherein said implants are configured for implantation across a disc space in the thoracolumbar region of the human spine.

121. An method for linking multiple spinal implants in the spine, comprising the steps of:

implanting a first spinal implant within a disc space between two adjacent vertebrae in a segment of the spine, said first spinal implant being adapted to contact both of the vertebrae adjacent to the disc space;

implanting a second spinal implant within the same disc space in which said first spinal implant is to be implanted, said second spinal implant being adapted to contact both of the vertebrae adjacent to the disc space; and connecting said implants with a connector.

122. The method of claim 121, wherein the implanting steps include implanting said implants having an end portion configured to couple to said connector.

123. The method of claim 121, wherein the implanting steps include implanting each of said implants having an end portion configured to receive said connector.

124. The method of claim 121, wherein the connecting step includes the sub-step of preventing rotation of said implants with said connector.

125. The method of claim 121, wherein the implanting steps include implanting said spinal implants including an artificial material other than bone.

126. The method of claim 121, wherein the implanting steps include implanting said implants across a disc space in the thoracolumbar region of the human spine.

* * * * *

UNITED STATES PATENT AND TRADEMARK OFFICE
CERTIFICATE OF CORRECTION

PATENT NO. : 6,136,001  
DATED : October 24, 2000  
INVENTOR(S) : Gary Karlin Michelson Page 1 of 1

It is certified that error appears in the above-identified patent and that said Letters Patent is hereby corrected as shown below:

Title page,  
Item [57], ABSTRACT,  
Line 14, change "deice" to -- device --;  
Line 17, change "pine" to -- spine --;

Column 18, claim 13,  
Line 5, change "an" to -- and --;

Column 18, claim 20,  
Line 1, after "18" insert -- , --;

Column 19, claim 40,  
Line 1, change "shank" to -- shanks --;

Column 20, claim 60,  
Line 5, change "vertebra" to -- vertebrae --;

Column 22, claim 89,  
Line 28, change "aligning" to -- attaching --; and

Column 24, claim 121,  
Line 1, change "An" to -- A --;

Signed and Sealed this

Twelfth Day of February, 2002

Attest:

JAMES E. ROGAN  
*Attesting Officer*   *Director of the United States Patent and Trademark Office*